US012011455B2

(12) United States Patent
Schoenecker et al.

(10) Patent No.: US 12,011,455 B2
(45) Date of Patent: Jun. 18, 2024

(54) ENHANCING PLASMIN ACTIVITY TO PREVENT SOFT TISSUE CALCIFICATION

(71) Applicant: Vanderbilt University, Nashville, TN (US)

(72) Inventors: Jonathan Schoenecker, Nashville, TN (US); Masato Yuasa, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 16/085,973

(22) PCT Filed: Mar. 17, 2017

(86) PCT No.: PCT/US2017/023099
§ 371 (c)(1),
(2) Date: Sep. 17, 2018

(87) PCT Pub. No.: WO2017/161354
PCT Pub. Date: Sep. 21, 2017

(65) Prior Publication Data
US 2019/0076459 A1 Mar. 14, 2019

Related U.S. Application Data

(60) Provisional application No. 62/309,821, filed on Mar. 17, 2016.

(51) Int. Cl.
*C12N 15/11* (2006.01)
*A61K 31/713* (2006.01)
*A61K 38/00* (2006.01)
*A61K 38/36* (2006.01)
*A61K 45/06* (2006.01)
*A61K 48/00* (2006.01)
*A61P 21/00* (2006.01)
*A61P 43/00* (2006.01)
*C12N 15/113* (2010.01)

(52) U.S. Cl.
CPC .......... *A61K 31/713* (2013.01); *A61K 38/005* (2013.01); *A61K 38/36* (2013.01); *A61K 45/06* (2013.01); *A61K 48/0016* (2013.01); *A61P 21/00* (2018.01); *A61P 43/00* (2018.01); *C12N 15/113* (2013.01); *C12N 2310/11* (2013.01); *C12N 2310/315* (2013.01); *C12N 2310/341* (2013.01); *C12N 2310/346* (2013.01)

(58) Field of Classification Search
CPC ....... A61P 21/00; A61K 38/005; A61K 38/36; A61K 48/0016; C12N 15/113
See application file for complete search history.

(56) References Cited

U.S. PATENT DOCUMENTS

| 5,304,383 A * | 4/1994 | Eibl ............... C12Y 304/21007 424/499 |
| 2007/0203220 A1* | 8/2007 | Crandall ................ A61K 31/56 514/419 |
| 2009/0254104 A1* | 10/2009 | Murray ................... A61L 27/54 606/151 |
| 2011/0027337 A1 | 2/2011 | Nielsen et al. |
| 2014/0171467 A1 | 6/2014 | Simard |
| 2016/0039943 A1 | 2/2016 | Reed |

FOREIGN PATENT DOCUMENTS

| WO | WO2013006372 A1 | 1/2013 | |
| WO | WO-2013036596 A2 * | 3/2013 | ............. A61P 11/00 |
| WO | WO2017077380 A1 | 5/2017 | |

OTHER PUBLICATIONS

Reed III et al., Synergistic fibrinolysis: Combined effects of plasminogen activators and an antibody that inhibits a2-antiplasmin, PNAS, 1990, vol. 87: 1114-1118 (Year: 1990).*
Ladermann et al., Supraspinatus Intramuscular Calcified Hematoma or Necrosis Associated with Tendon Tear. Case Rep Orthop. 2015, vol. 2015:496313. PDF File: p. 1-4.
GENBANK_BF659485, maa30110.y1 NCI_CGAP_Li10 Mus musculus CDNA clone IMAGE:3812515 5- similar to SW: A2AP_MOUSE Q61247 ALPHA-2-ANTIPLASMIN Precursor ;, mRNA sequence. Last Update: Jun. 8, 2011. [online]. [Retrieved on Jun. 9, 2017]. Retrieved from the Internet: <URL:https://www.ncbi.nlm.nih.gov/nucest/BF659485> Title; and Sequence, the region between nucleotides 226-207.
Alessandrino et al., Complications of muscle injuries. J Ultrasound. 2013, vol. 16(4), p. 215-22. Entire documentation, especially Abstract; p. 215, col. 2, middle para; and p. 218.
Mignemi et al., Plasmin Prevents Dystrophic Calcification After Muscle Injury. J Bone Miner Res. 2017, vol. 32(2), p. 294-308.
Covey, D. C., Combat orthopaedics: a view from the trenches. The Journal of the American Academy of Orthopaedic Surgeons 14, S10 (2006).
Gajewski, et al., The United States Armed Forces Amputee Patient Care Program. The Journal of the American Academy of Orthopaedic Surgeons 14, S183 (2006).
Nelson, et al., Heterotopic ossification following burn injury: the role of stem cells. Journal of burn care & research : official publication of the American Burn Association 2012, 33, 463-470.
Forsberg et al., Heterotopic ossification in high-energy wartime extremity injuries: prevalence and risk factors. The Journal of bone and joint surgery. American vol. 91, 1084 (2009).
Urist, M. R., Bone: formation by autoinduction. Science 150, 893 (Nov. 12, 1965).

(Continued)

Primary Examiner — Ekaterina Poliakova-Georgantas
(74) Attorney, Agent, or Firm — Stites & Harbison PLLC; Richard S. Myers, Jr.

(57) ABSTRACT

A method for reducing or substantially preventing soft tissue calcification is provided. The method includes administering at least one of a downregulator of at least one plasmin inhibitors and plasmin(ogen) to a subject in need thereof, wherein the at least one plasmin inhibitor includes alpha2-antiplasmin. Further disclosed is a method comprises administering the compound subsequent to muscle injury, and the method further comprising administering an antifibrinolytic.

11 Claims, 29 Drawing Sheets

(56) References Cited

OTHER PUBLICATIONS

Urist, et al., Solubilized and insolubilized bone morphogenetic protein. Proceedings of the National Academy of Sciences of the United States of America 76, 1828 (Apr. 1979).
Wozney et al., Novel regulators of bone formation: molecular clones and activities. Science 242, 1528 (Dec. 16, 1988).
Kaplan et al., Fibrodysplasia ossificans progressiva. Best practice & research. Clinical rheumatology 22, 191 (Mar. 2008).
Mitchell, et al., The genetics of heterotopic ossification: insight into the bone remodeling pathway. J Orthop Trauma 24, 630 (Sep. 2010).
Chalmers, et al., Observations on the induction of bone in soft tissues. The Journal of bone and joint surgery. British vol. 57, 36 (1975).
Agarwal et al., Inhibition of Hif1alpha prevents both trauma-induced and genetic heterotopic ossification. Proceedings of the National Academy of Sciences of the United States of America 113, E338 (Jan. 19, 2016).
Fleish, et al., Mechanisms of calcification: role of collagen, polyphosphates, and phosphatase. Am J Physiol 200, 1296 (Jun. 1961).
Gillman, et al., Histochemical and chemical studies of calciferol-induced vascular injuries. Br J Exp Pathol 41, 1 (Feb. 1960).
Fleisch, et al., Effect of pyrophosphate on dissolution of hydroxyapatite and its possible importance in calcium homeostasis. Proc Soc Exp Biol Med 122, 317 (Jun. 1966).
Goodman et al., Pseudoxanthoma Elasticum: A Clinical and Histopathological Study. Medicine (Baltimore) 42, 297 (Sep. 1963).
Yuan et al., Osteoinduction by calcium phosphate biomaterials. J Mater Sci Mater Med 9, 723 (Dec. 1998).
Ripamonti, U., Osteoinduction in porous hydroxyapatite implanted in heterotopic sites of different animal models. Biomaterials 17, 31 (Jan. 1996).
Le Nihouannen et al., Ectopic bone formation by microporous calcium phosphate ceramic particles in sheep muscles. Bone 36, 1086 (Jun. 2005).
Cohen et al., Critical role of activated protein C in early coagulopathy and later organ failure, infection and death in trauma patients. Annals of surgery 255, 379 (Feb. 2012).
Enderson, J. P. Chen, R. Robinson, K. I. Maull, Fibrinolysis in multisystem trauma patients. The Journal of trauma 31, 1240 (Sep. 1991).
Sorensen, Levels of fibrinolytic activators and inhibitors in plasma after severe trauma. Blood coagulation & fibrinolysis : an international journal in haemostasis and thrombosis 5, 43 (Feb. 1994).
Boudjeltia et al., Relationship between CRP and hypofibrinolysis: Is this a possible mechanism to explain the association between CRP and outcome in critically ill patients? Thrombosis journal 2, 7 (Sep. 30, 2004).
Deryugina, J. P. Quigley, Cell surface remodeling by plasmin: a new function for an old enzyme. Journal of biomedicine & biotechnology 2012, 564259 (2012).
Gu et al., Plasminogen K5 activates mitochondrial apoptosis pathway in endothelial cells by regulating Bak and Bcl-x (L) subcellular distribution. Apoptosis : an international journal on programmed cell death 16, 846 (Aug. 2011).
Creemers et al., Disruption of the plasminogen gene in mice abolishes wound healing after myocardial infarction. The American journal of pathology 156, 1865 (Jun. 2000).
Gong, et al., Hoover-Plow, Plasminogen regulates cardiac repair after myocardial infarction through its noncanonical function in stem cell homing to the infarcted heart. Journal of the American College of Cardiology 63, 2862 (Jul. 1, 2014).
V. A. Ploplis et al., Effects of disruption of the plasminogen gene on thrombosis, growth, and health in mice. Circulation 92, 2585 (Nov. 1, 1995).
Drixler et al., Plasminogen mediates liver regeneration and angiogenesis after experimental partial hepatectomy. The British journal of surgery 90, 1384 (Nov. 2003).
Romer et al., Impaired wound healing in mice with a disrupted plasminogen gene. Nature medicine 2, 287 (Mar. 1996).
Yuasa et al., Fibrinolysis is essential for fracture repair and prevention of heterotopic ossification. J Clin Invest 125, 3117 (Aug. 3, 2015).
Bezerra et al., Plasminogen deficiency leads to impaired remodeling after a toxic injury to the liver. Proceedings of the National Academy of Sciences of the United States of America 96, 15143 (Dec. 21, 1999).
Baker BF, Lot SS, Condon TP, et al. 2'-O-(2-Methoxy)ethyl-modified anti-intercellular adhesion molecule 1 (ICAM-1) bligonucleotides selectively increase the ICAM-1 mRNA level and inhibit formation of the ICAM-1 translation initiation complex in human umbilical vein endothelial cells. The Journal of biological chemistry. 1997;272(18): 11994-2000.
Deconinck, B. Dan, Pathophysiology of duchenne muscular dystrophy: current hypotheses. Pediatric neurology 36, 1 (Jan. 2007).
Suelves et al., uPA deficiency exacerbates muscular dystrophy in MDX mice. The Journal of cell biology 178, 1039 (Sep. 10, 2007).
Lounev et al., Identification of progenitor cells that contribute to heterotopic skeletogenesis. The Journal of bone and joint surgery. American vol. 91, 652 (Mar. 1, 2009).
Cole et al., Fibrin accumulation secondary to loss of plasmin-mediated fibrinolysis drives inflammatory osteoporosis in mice. Arthritis & rheumatology 66, 2222 (Aug. 2014).
Lluis et al., Urokinase-dependent plasminogen activation is required for efficient skeletal muscle regeneration in vivo. Blood 97, 1703 (Mar. 15, 2001).
Suelves et al., Plasmin activity is required for myogenesis in vitro and skeletal muscle regeneration in vivo. Blood 99, 2835 (Apr. 15, 2002).
Urist, et al., Bone Cell Differentiation and Growth Factors Science 220, 680 (May 13, 1983).
Douglas et al., Enzymatically induced mineralization of platelet-rich fibrin. Journal of biomedical materials research. Part A 100, 1335 (May 2012).
Russell, R. G., Bisphosphonates: the first 40 years. Bone 49, 2 (Jul. 2011).
Bugge et al., Loss of fibrinogen rescues mice from the pleiotropic effects of plasminogen deficiency. Cell 87, 709 (Nov. 15, 1996).
Vidal et al., Amelioration of Duchenne muscular dystrophy in mdx mice by elimination of matrix-associated fibrin-driven Inflammation coupled to the alphaMbeta2 leukocyte integrin receptor. Human molecular genetics 21, 1989 (May 1, 2012).
Kanno et al., Lack of alpha2-antiplasmin improves cutaneous wound healing via over-released vascular endothelial growth factor-induced angiogenesis in wound lesions. Journal of thrombosis and haemostasis : JTH 4, 1602 (Jul. 2006).
Khalil, et al., Plasmin regulates the activation of cell-associated latent TGF-beta 1 secreted by rat alveolar macrophages after in vivo bleomycin injury. American journal of respiratory cell and molecular biology 15, 252 (Aug. 1996).
Ploplis, et al., Plasminogen deficiency differentially affects recruitment of inflammatory cell populations in mice. Blood 91, 2005 (Mar. 15, 1998).
Roth et al., Plasmin modulates vascular endothelial growth factor-A-mediated angiogenesis during wound repair. Am J Pathol 168, 670 (Feb. 2006).
Schoenecker et al., 2010 Young Investigator Award winner: Therapeutic aprotinin stimulates osteoblast proliferation put inhibits differentiation and bone matrix mineralization. Spine 35, 1008 (Apr. 20, 2010).
Yee, et al., Plasminogen-dependent activation of latent transforming growth factor beta (TGF beta) by growing cultures of osteoblast-like cells. Journal of cellular physiology 157, 528 (Dec. 1993).
Christensen, et al., Osteopontin is cleaved at multiple sites close to its integrin-binding motifs in milk and is a novel substrate for plasmin and cathepsin D. The Journal of biological chemistry. 2010;285(11):7929-37.
Herrmann et al., Clearance of fetuin-A-containing calciprotein particles is mediated by scavenger receptor-A. Circulation research 111, 575 (Aug. 17, 2012).

(56) References Cited

OTHER PUBLICATIONS

Steitz et al., Osteopontin inhibits mineral deposition and promotes regression of ectopic calcification. Am J Pathol 161, 2035 (Dec. 2002).

Ploplis, et al., Plasminogen deficiency differentially affects recruitment of inflammatory cell populations in mice. Blood 91, 2005 (1998).

Das, S. Ganapathy, M. Settle, E. F. Plow, Plasminogen promotes macrophage phagocytosis in mice. Blood 124, 679 (Jul. 31, 2014).

Henson, Peter M., The immunologic release of constituents from neutrophil leukocytes. II. Mechanisms of release during phagocytosis, and adherence to nonphagocytosable surfaces. J Immunol 107, 1547 (Dec. 1971).

McNally, et al., Macrophage fusion and multinucleated giant cells of inflammation. Advances in experimental medicine and biology 713, 97 (2011).

Yu et al., BMP type I receptor inhibition reduces heterotopic [corrected] ossification. Nature medicine 14, 1363 (Dec. 2008).

Schneiderman et al., Increased type 1 plasminogen activator inhibitor gene expression in atherosclerotic human arteries. Proceedings of the National Academy of Sciences of the United States of America 89, 6998 (Aug. 1, 1992).

Eitzman, et al.,, Plasminogen activator inhibitor-1 deficiency protects against atherosclerosis progression in the mouse carotid artery. Blood 96, 4212 (Dec. 15, 2000).

Xiao et al., Plasminogen deficiency accelerates vessel wall disease in mice predisposed to atherosclerosis. Proceedings of the National Academy of Sciences of the United States of America 94, 10335 (Sep. 16, 1997).

Eren et al., PAI-1-regulated extracellular proteolysis governs senescence and survival in Klotho mice. Proceedings of the National Academy of Sciences of the United States of America 111, 7090 (May 13, 2014).

Tsuji et al., BMP2 activity, although dispensable for bone formation, is required for the initiation of fracture healing. Nat Genet 38, 1424 (Dec. 2006).

Cooley, et al., The effects of transplantation and x-irradiation on the repair of fractured bones. Am J Anat 102, 167 (Mar. 1958).

De Luca, et al., Retinoic acid is a potent regulator of growth plate chondrogenesis. Endocrinology 141, 346 (Jan. 2000).

Lewis, et al., Inhibition of limb chondrogenesis in vitro by vitamin A: alterations in cell surface characteristics. Dev Biol 64, 31 (May 1978).

Li et al., Concentration of bisphosphonate (incadronate) in callus area and its effects on fracture healing in rats. Journal of bone and mineral research : the official journal of the American Society for Bone and Mineral Research 15, 2042 (Oct. 2000).

Moore, et al., Validation of Radiography-Based Quantification Designed to Longitudinally Monitor Cardiotoxin-Induced Heterotopic Ossification in a Murine Model. PloS one, (Submitted and in Review Feb. 12, 2016).

Flick, et al., Fibrin(ogen)-alpha M beta 2 interactions regulate leukocyte function and innate immunity in vivo. Experimental biology and medicine 229, 1105 (Dec. 2004).

Hettiaratchy, et al., Initial management of a major burn: I-overview. BMJ 328, 1555 (Jun. 26, 2004).

Molligan, et al. Influence of Bone and Muscle Injuries on the Osteogenic Potential of Muscle Progenitors: Contribution of Tissue Environment to Heterotopic Ossification. Stem Cells Transl Med. 2016.

\* cited by examiner

Von Kossa

14 DPI

28 DPI

H&E

14 DPI

28 DPI

Safranin-O

14 DPI

28 DPI

TRAP

14 DPI    28 DPI

Von Kossa

14 DPI    28 DPI

H&E

14 DPI    28 DPI

Safranin-O

14 DPI            28DPI

TRAP

14 DPI            28 DPI

ENHANCING PLASMIN ACTIVITY TO PREVENT SOFT TISSUE CALCIFICATION

RELATED APPLICATIONS

This application is a § 371 National State Application of PCT/US2017/023099 filed Mar. 17, 2017, which claims the benefit of U.S. Provisional Application Ser. No. 62/309,821, filed Mar. 17, 2016, the entire disclosure of which is incorporated herein by this reference.

GOVERNMENT INTEREST

This invention was made with government support under Grant Nos. 5T32 HL007751, 5T32 GM007628, 1R03AR065762-01A1, S10RR027631, and 3T32DK007061-41S1 awarded by the National Institutes of Health. The government has certain rights in the invention.

TECHNICAL FIELD

The presently-disclosed subject matter generally relates to compounds and methods for preventing soft tissue calcification. In particular, certain embodiments of the presently-disclosed subject matter relate to methods for increasing plasmin(ogen) activity to reduce or prevent soft tissue calcification.

BACKGROUND

The process of ossification (FIG. 1A) provides bone which is essential for support and protection. The formation and maintenance of bone is promoted by calcium and phosphate, which are also required for proper cellular function and signaling. concentrations in the extracellular space near their saturation point. While concentrations of calcium and phosphate at their saturation points when circulating in plasma are ideal for maintaining bone integrity, they can aberrantly aggregate in soft tissue, especially following injury, a process referred to as dystrophic (or pathologic) calcification.

Dystrophic calcification (i.e., the deposition of calcium phosphate crystals) is injurious, imposing chronic inflammation and potentially loss of the afflicted organ's function. It is involved in a myriad of disease processes, such as Alzheimer's disease, renal calcinosis, and breast cancer (FIG. 1B). Dystrophic calcification also commonly occurs in muscle following injury, secondary to exceptionally high concentrations of calcium and phosphate required for muscle function. Calcification of smooth muscle in the vascular wall is a pathophysiologic component of atherosclerosis. Calcification of skeletal muscle is a pathophysiologic consequence of a disease commonly referred to as heterotopic ossification (HO, formation of mature bone tissue within soft tissues), which occurs following severe injuries such as burn, blast, neurological injury, and/or certain orthopaedic procedures.

With respect to skeletal muscle calcification, when muscle is injured, resident mesenchymal stem cells normally perform myogenesis resulting in functionally competent muscle. However, in certain circumstances, injured muscle can develop dystrophic calcification (FIG. 2). As noted above, dystrophic calcification results in chronic inflammation and failed muscle regeneration, causing pain and a variable loss of limb function. Additionally, dystrophic calcification provides a microenvironment in which resident mesenchymal stem cells differentiate into osteoblasts instead of myocytes and develop heterotopic ossification (HO). HO results in complete loss of muscle function, and if surrounding a joint, loss of that limbs function.

Together, muscle dystrophic calcification and HO are a major source of morbidity and health care expenditure following severe burn, blast, or neurologic injuries as well as certain orthopaedic procedures. Although estimates vary, between 10-80% of patients suffer from various forms of HO after traumatic injury, and trauma induced muscle calcification has complicated more than 60% of severe wartime extremity orthopaedic injuries during the Afghanistan and Iraqi conflicts. Surgical excision is extensive, morbid and often incomplete. While severe traumatic injury appears to alter the tissue microenvironment in injured skeletal muscle so as to promote osteogenesis over myogenesis, independent of any known genetic predisposition in bone morphogenetic protein (BMP) signaling, the molecular pathogenesis of trauma-induced muscle calcification, both dystrophic calcification and HO, is uncertain.

Due to the poor understanding of pathophysiology in these conditions, current therapies are either insufficient or have unacceptable adverse effects on bone integrity and regeneration. For example, Urist first demonstrated that transplanting demineralized bone into muscle is sufficient to provoke HO. The osteoinductive factor in these experiments was revealed as bone morphogenic protein (BMP), one of many growth factors of the transforming growth factor (TGF) family laden in bone. Based on these observations, a widely held and long-standing hypothesis emerged that HO develops when injured muscle is exposed to a bone regenerative microenvironment. However, most fractures penetrate muscle and do not result in HO and HO often forms in skeletal muscle surrounding intact bone remote from the site of injury. These clinical observations conflict with this hypothesis and instead indicate that traumatic introduction of bone into muscle is not sufficient or essential to provoke HO. Other pathogenic factors appear to be required.

Subsequently, it was determined that HO is not only associated with severe trauma, but also can be linked to specific genetic mutations, such as those genes encoding osteoinductive signaling factors, such as BMP signaling, that promote HO in fibrodysplasia ossificans progressiva (FOP). Despite the clear genetic etiology of FOP, mutations in BMP signaling pathways have not been observed in patients with trauma-induced HO. Instead, severe trauma appears to alter the tissue microenvironment in injured skeletal muscle so as to promote osteogenesis over myogenesis, independent of any known genetic predisposition. In accordance, Chalmers concluded that traumatic HO requires an inducing stimulus (trauma), osteogenic precursor cells, and an osteoinductive tissue microenvironment. One finding consistent with this view is that persistent signaling through the hypoxia inducible factor pathway is osteoinductive as it drives invading mesenchymal stem cells (MSCs) toward endochondral bone formation in injured muscle.

However, HO initiating osteoinductive factors within the soft tissue microenvironment are not limited to bone related growth factor signaling. In plasma, calcium and phosphate are at their saturation point and, if stimulated by a nucleating factor such as collagen, rapidly form biological crystals; most notably, hydroxyapatite. Following injury, exposure of nucleating matrices with saturating concentrations of these ions predisposes for untimely aggregation in soft tissue such as muscle, skin, and blood vessels. If unresolved, these mineral depositions are sufficient to drive endochondral ossification and the formation of mature HO. Therefore, even without inappropriate activation of bone related growth factors, HO may result from the loss of one or more factors that protects against calcium and phosphate formation of dystrophic calcification within injured muscle.

In another attempt, studies have focused on circulating levels of pyrophosphate. Pyrophosphate directly inhibits calcium and phosphate aggregation, preventing in vivo mineralization. Circulating levels of pyrophosphate are maintained by "pyrophosphate pumps," which in turn provide the front line defense against soft tissue calcification. It follows that genetic mutations to elements of the pyrophosphate pump are considered a potential underlying cause of soft tissue calcification disorders such as Pseudoxanthoma elasticum (PXE—ABCC6 mutation) and generalized arterial calcification of infancy (GACI—ENPP1 mutation). If hypo-pyrophosphatemia were identified as the underlying cause of soft tissue calcification in PXE and GACI, a logical treatment would be to replenish pyrophosphate. However, pyrophosphate is quickly metabolized during gut absorption, thus necessitating an alternative route of supplementation. To address this, researchers, such as Li et al., have turned to non-hydrolyzable pyrophosphate analogs, bisphosphonates, to potentially prevent aberrant mineralization in these patients by supplementing the deficient pyrophosphate system.

Bisphosphonates are a powerful family of pharmaceuticals utilized by clinicians for more than 40 years to prevent osteoporosis. These stable forms of pyrophosphate freely pass into cells and act as effective inhibitors of the HMG-CoA reductase pathway. Bisphosphonates have pleiotropic effects on cellular function, most notably attenuating osteoclast activity and reducing these cells' ability to resorb bone. That said, industrial use of bisphosphonates to protect against aberrant mineralization predates their use to preserve bone by at least a century. Bisphosphonates were first used to "soften" public water supplies in the 1800s thereby preventing calcification of pipes. Additionally, the first clinical papers regarding bisphosphonates and their uses in vivo in the 1960s focused on their ability to prevent calcium and phosphate aggregation. Despite the well-documented anti-mineralization properties of bisphosphonates, their predominate clinical application has instead been concentrated on their anti-bone restorative properties.

In view thereof, Li et al. investigated the efficacy of bisphosphonate administration on mice with a deficiency of ABCC6 that are prone to developing spontaneous calcification in soft tissues. Specifically, the Li et al. determined that even oral administration of bisphosphonates has the capacity to protect soft tissue from calcification in these "PXE" mice. This work represents an integral step toward the clinical application of bisphosphonates, as it not only supports the concept that the soft tissue calcification caused by a loss of ABCC6 is a result of a pyrophosphate deficiency, but it also gives hope that bisphosphonates are effective means of replenishing this deficiency.

Despite these findings, the risk of bisphosphonate treatment in these patients must be carefully considered. Bisphosphonates are excellent at preventing the establishment of mineralization, but they are also known to strongly bind to pre-formed hydroxyapatite, such as bone, and persist in these areas for up to 10 years following treatment. Considering that most PXE patients already possess soft tissue calcification within their skin or retina, it is unknown what clinical effect administering bisphosphonates will have since bisphosphonates will also bind to sites of pre-existing soft tissue calcification, as they do in bone. Additionally, it is unknown what effect the bisphosphonate inhibition of the HMG-CoA reductase pathway will have on the cells of this soft tissue environment, such as dermal or retinal cells. Currently known short-term side effects include: esophageal irritation, acute phase response activation, ocular inflammation, hypocalcemia, acute renal damage, and musculoskeletal pain. Long-term safety concerns also have been reported that include osteonecrosis of the jaw, and atypical femur fractures. Thus there remains a concern for both short-term and long-term side effects of bisphosphonates.

Without a complete understanding of the molecular mechanism leading to trauma-induced muscle calcification, current and proposed treatments for skeletal muscle calcification all have the undesirable adverse effect of disrupting systemic bone homeostasis and inhibiting fracture repair. Accordingly, there remains a need for a compound and/or method of protecting against pathological muscle calcification while promoting normal bone biology.

SUMMARY

The presently-disclosed subject matter meets some or all of the above-identified needs, as will become evident to those of ordinary skill in the art after a study of information provided in this document.

This summary describes several embodiments of the presently-disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this summary or not. To avoid excessive repetition, this summary does not list or suggest all possible combinations of such features.

In some embodiments, the presently-disclosed subject matter includes a method for reducing or substantially preventing soft tissue calcification in a subject, comprising administering at least one of a downregulator of at least one plasmin inhibitors and plasmin(ogen). In one embodiment, the at least one plasmin inhibitor includes α2-antiplasmin. In another embodiment, the downregulator is an α2-antiplasmin antisense oligonucleotide. In one embodiment, the plasmin(ogen) is natural plasmin(ogen). In another embodiment, the plasmin is recombinant plasmin(ogen). In some embodiment, the method further comprises administering the compound at the time of or subsequent to muscle injury.

Further features and advantages of the presently-disclosed subject matter will become evident to those of ordinary skill in the art after a study of the description, figures, and non-limiting examples in this document.

Soft Tissue Calcification Score (7-DPI): depleting the plasmin inhibitor α2AP (α2AP$^{ASO}$), but not fibrinogen (Plg$^{+/-}$Fbg$^{Low}$ and Fbg$^{-/-}$Plg$^{Low}$) prevented soft tissue calcification. Medians and interquartile ranges are shown (N≥4;*P<0.05; Mann-Whitney test vs. Plg$^{+/-}$ control mice).

Figure 8A:
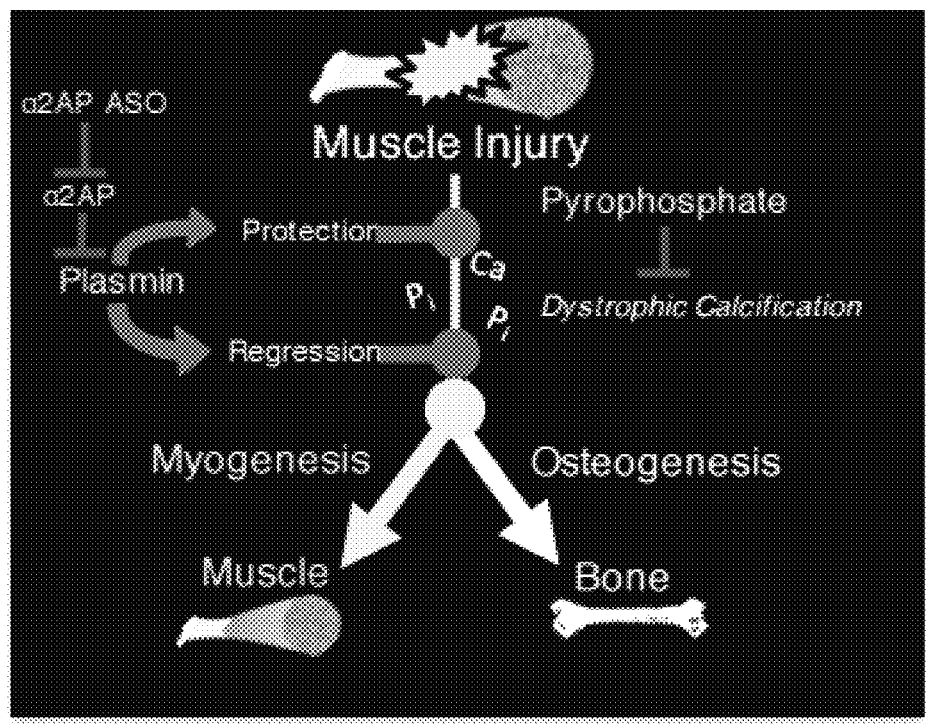
Figure 8B:
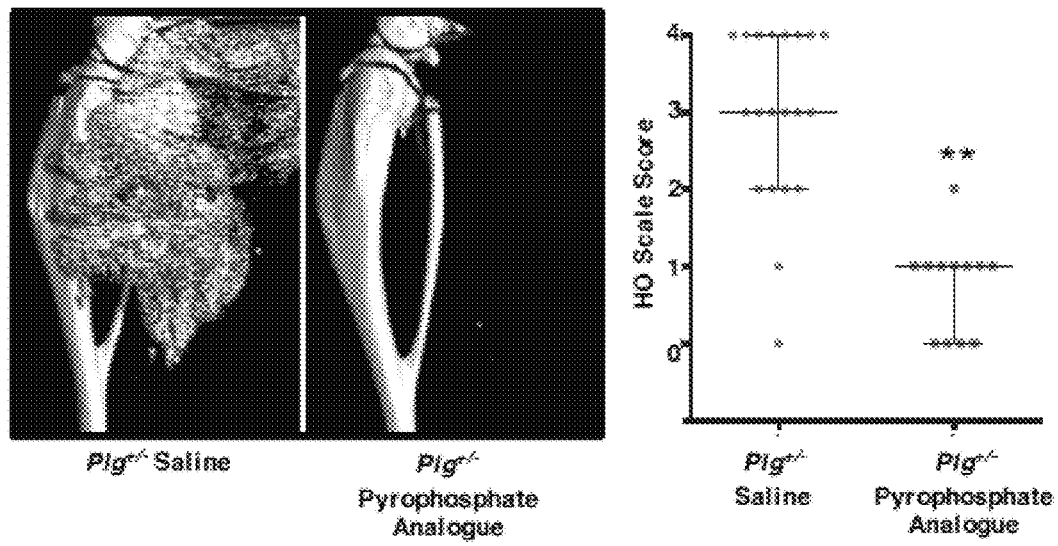
Figure 8C:
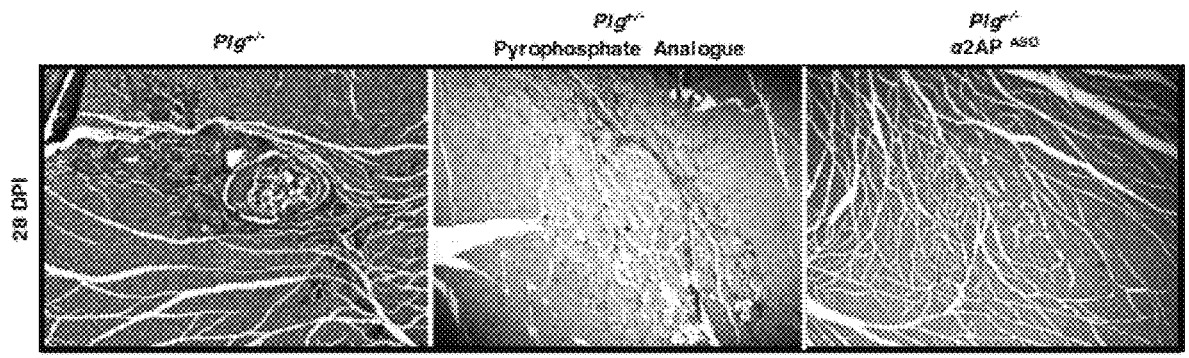

FIGS. 8A-C show graphs and images illustrating pyrophosphate treatment preventing soft tissue calcification HO in the setting of plasmin deficiency and muscle injury. (A) Proposed mechanism for selected therapeutic rescue of plasmin deficiency-associated soft tissue calcification and HO. Depleting the plasmin inhibitor α2AP (α2AP$^{ASO}$) increases plasmin activity. Supplementation of endogenous pyrophosphate with non-hydrolysable pyrophosphate analogues confers additional protection against dystrophic calcification. (B) μCT reconstructions and Soft Tissue Calcification Scores of lower limb of CTX-injured Plg$^{+/-}$ mouse pretreated with pyrophosphate analogue demonstrated marked reduction of soft tissue calcification compared to controls 7 DPI. Medians and interquartile ranges are shown. (N≥12;**P<0.001, Mann-Whitney test. (C) H&E stains of CTX-injured Plg$^{+/-}$ mice 28 DPI. Pyrophosphate analogue treatment (Plg$^{+/-}$ pyrophosphate analogue) and depletion of α2AP (Plg$^{+/-}$α2AP$^{ASO}$) prevented HO in the setting of partial plasminogen deficiency (Plg$^{+/-}$). However, resolution of necrotic muscle occurred with depletion of α2AP and not pyrophosphate analogue treatment.

FIGS. 9A-E. Burn Depletion of Plasmin Correlates with Injury Severity. (A) Quantification of plasma plasminogen concentration by ELISA from human burn patients: note significantly decreased plasminogen levels at presentation and 3 DPI compared to non-burned controls. (N≥4;*P<0.05; Mann-Whitney test) (B) Quantification of plasma plasmin activity by substrate cleavage: note significantly decreased plasmin activity at presentation and 3 DPI compared to non-burned controls (N>4,*P=0.0003, Mann-Whitney test) and day 3 (N=11; *P=0.0003; Mann-Whitney test). (C) Plasmin activity correlation with plasminogen antigen in plasma of burned patients (N=29; P<0.0001; Spearman r=0.87). (D) Correlation of burn imposed deficiency of plasmin activity (3 DPI) with total body surface area (TBSA) burned (N=17;P=0.0014; Spearman r=-0.70) and (E) injury severity quantified by APACHE II (N=17; **P<0.0001; Spearman r=-0.86). (Dotted lines indicate the 95% confidence interval for the linear regression curve).

FIGS. 10A-D. Cutaneous burn with muscle injury is sufficient to cause plasmin depletion, HO and is prevented by restoring plasmin activity. (A) Quantification of plasma plasminogen concentration by ELISA 3 DPI: Note 30% TBSA burn with muscle injury (CTX), but not CTX alone, significantly decreased plasminogen levels compared to control mice (WT). Burn imposed plasminogen depletion was comparable to mice with a partial plasminogen deficiency (Plg$^{+/-}$ mice and Plg$^{Low*}$) but greater than a complete plasminogen deficiency (Plg$^{-/-}$). (N≥6;*P<0.05; Mann-Whitney test comparing WT to experimental groups). (B) uCT reconstructions and HO quantification of the lower limb of WT mice after burn injury alone and burn with concomitant muscle (CTX) injury: note the significant HO in the setting of combined burn and muscle injury. Medians and interquartile ranges are shown (N≥4;*P<0.05; Mann-Whitney test) (C) μCT reconstructions and HO quantification of lower limb of combined burned and CTX injected WT mice demonstrated significant reduction of HO when pretreated with a pyrophosphate analogue. Median and interquartile range are shown. (N≥4;P<0.001, Mann-Whitney test). (D) μCT reconstructions and HO quantification of the lower limb of WT mice after cutaneous burn followed by CTX-induced muscle injury demonstrated significant reduction of HO when treated with α2AP$^{ASO}$. (N≥10;P<0.001; Mann-Whitney test).

Figure 11A:
Figure 11B:
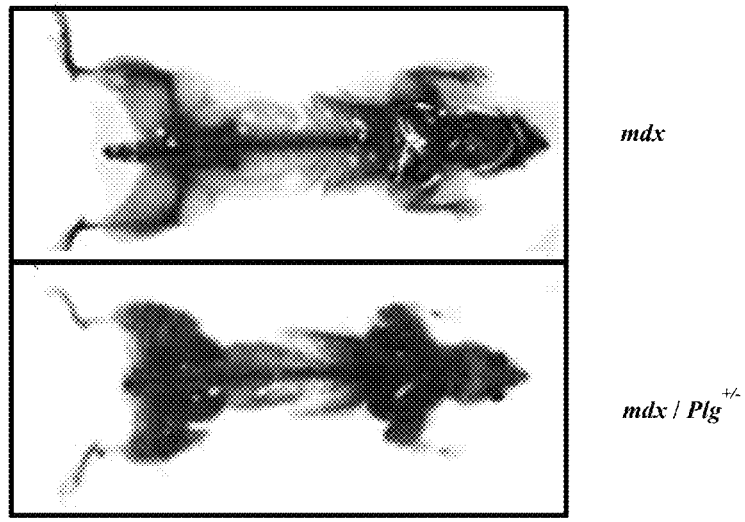

FIGS. 11A-B show images illustrating ossification and calcification.

FIGS. 12A-H show graphs and images illustrating histologic quantitation of muscle healing in WT and Plg$^{+/-}$ mice.

Figure 13A:
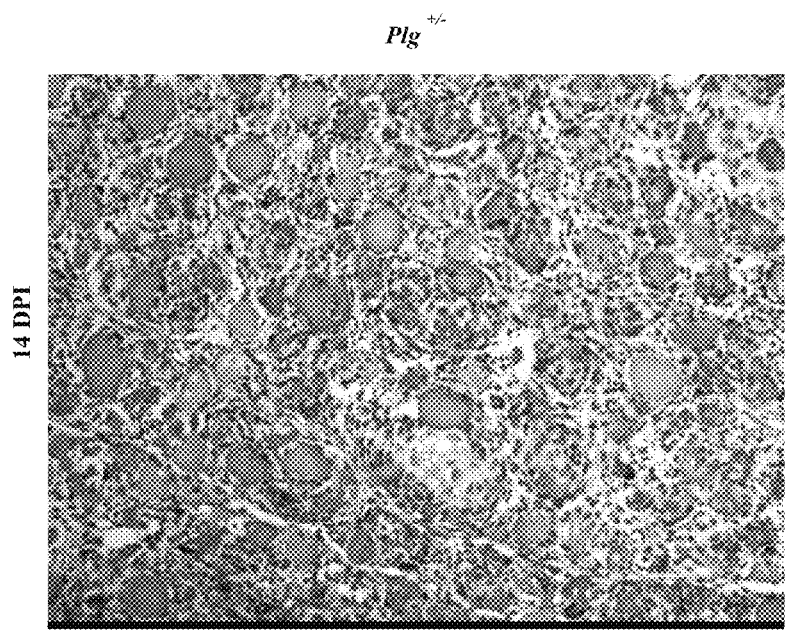
Figure 13B:
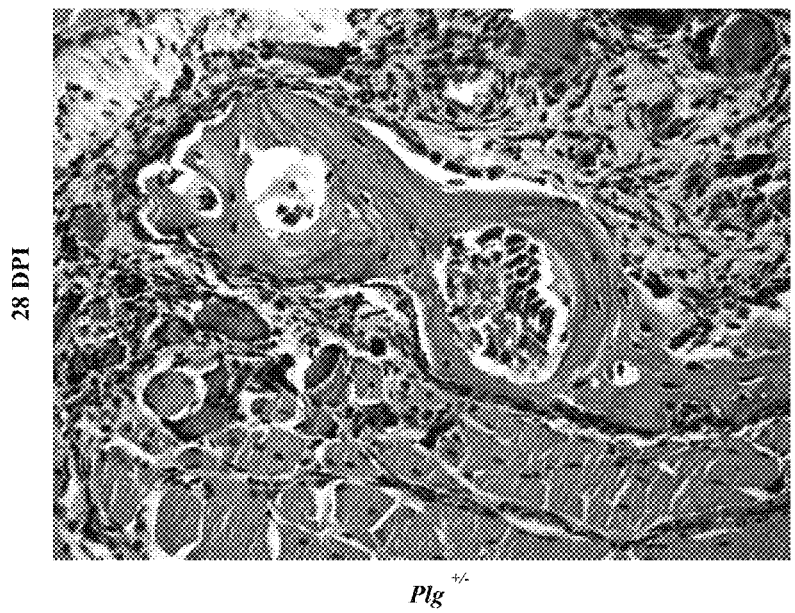

FIGS. 13A-B show images illustrating the evolution of dystrophic calcifications into HO as evaluated histologically.

Figure 14:
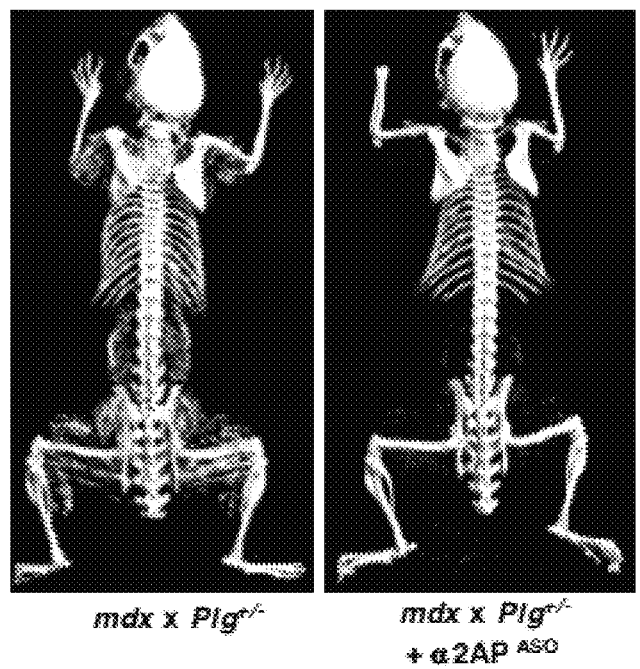

FIG. 14 shows images illustrating that HO in continuous muscle injury and plasminogen deficiency can be rescued by increasing plasmin activity with α2-Antiplasmin ASO.

FIGS. 15A-E show graphs and images illustrating histological analysis and quantification of muscle healing in Plg$^{+/-}$ mice treated with either Control ASO or α2-Antiplasmin ASO.

DESCRIPTION OF EXEMPLARY EMBODIMENTS

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

Unless defined otherwise, all technical and scientific terms used herein have the same meaning as is commonly understood by one of skill in the art to which the invention(s) belong. All patents, patent applications, published applications and publications, GenBank sequences, databases, websites and other published materials referred to throughout the entire disclosure herein, unless noted otherwise, are incorporated by reference in their entirety. In the event that there are a plurality of definitions for terms herein, those in this section prevail. Where reference is made to a URL or other such identifier or address, it understood that such identifiers can change and particular information on the internet can come and go, but equivalent information can be found by searching the internet. Reference thereto evidences the availability and public dissemination of such information.

Although any methods, devices, and materials similar or equivalent to those described herein can be used in the practice or testing of the presently-disclosed subject matter, representative methods, devices, and materials are now described.

As used herein, the abbreviations for any protective groups, amino acids and other compounds, are, unless indicated otherwise, in accord with their common usage, recognized abbreviations, or the IUPAC-IUB Commission on Biochemical Nomenclature (see, Biochem. (1972) 11(9): 1726-1732).

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the term "plasmin(ogen)" refers to either plasmin or plasminogen.

In some embodiments, the presently-disclosed subject matter includes methods for reducing, substantially preventing, or preventing soft tissue calcification. As used herein, the term "soft tissue" refers to any tissue which is not hard, mineralized, or calcified tissue. For example, soft tissue may refer to muscle, skin, blood vessels, tendons, ligaments, fascia, fibrous tissue, fat, nerves, or a combination thereof. Although primarily described herein with respect to muscle, as will be understood by those of ordinary skill in the art, soft tissue is not so limited and may include any other soft tissue encompassed by the definition above.

In some embodiments, the method for reducing, substantially preventing, or preventing soft tissue calcification includes increasing and/or enhancing plasmin(ogen) activity. In one embodiment, the increasing and/or enhancing of plasmin(ogen) activity may include administering a downregulator of one or more plasmin inhibitors that is effective for reducing, substantially preventing, or preventing soft tissue calcification in a subject. In another embodiment, the plasmin inhibitor includes α2-antiplasmin (α2AP). In a further embodiment, the downregulator of the one or more plasmin inhibitors includes an antisense oligonucleotide (ASO), such as, but not limited to, an α2AP ASO (α2AP$^{ASO}$). Other downregulators include, but are not limited to, competitive inhibitors that bind to the active site of the one or more plasmin inhibitors, non-competitive inhibitors that reduce activity of the one or more plasmin inhibitors, and/or irreversible inhibitors that covalently modify the one or more plasmin inhibitors.

Without wishing to be bound by theory, it is believed that decreased levels of plasmin(ogen) impede or inhibit urokinase plasminogen activator (uPA)-mediated extravascular activation of plasmin, which is required for regulation of muscle calcification. As such, administering a downregulator of the one or more plasmin inhibitors increases the availability of plasmin, which in turn decreases or eliminates soft tissue calcification. Accordingly, the method disclosed herein is applicable to acute or chronic injury events, which systemically consume an inordinate amount of plasminogen, as well as diseases that reduce the availability and/or amount of plasmin(ogen). For example, the methods disclosed herein are applicable to injuries such as burns or other traumatic injury that consume plasminogen, as well as conditions involving impaired fibrinolysis and diseases which affect plasminogen production and/or availability. In addition to being the principal protease of the fibrinolytic system, plasmin, converted from its zymogen plasminogen, serves as an activator of tissue remodeling factors such as matrix metalloproteinase and growth factors such as TGFβand VEGF. As such, the methods disclosed herein are also applicable to improving fracture repair, preventing trauma induced osteoporosis, reducing or eliminating progression of atherosclerosis, reducing or eliminating renal calcinosis, or a combination thereof.

More specifically, in some embodiments, the method includes administering plasmin(ogen) and/or a downregulator of one or more plasmin inhibitors following injury. In some embodiments, the plasmin(ogen) and/or downregulator is administered prior to, at the time of, or subsequent to injury. In some embodiments, providing a predetermined amount of plasmin(ogen) activity reduces, substantially prevents, prevents, and/or protects against the formation of dystrophic calcification following muscle injury. In some embodiments, providing a predetermined amount of plasmin(ogen) activity reduces, substantially prevents, prevents, heterotopic ossification following muscle injury. In some embodiments, the presently-disclosed subject matter includes methods of plasmin-mediated proteolysis in muscle regeneration.

Additionally or alternatively, in some embodiments, the presently-disclosed method includes administering plasmin. For example, in place of or in addition to administering a downregulator of one or more plasmin inhibitors, the method may include administering an amount of plasmin(ogen) that is effective for reducing, substantially preventing, or preventing dystrophic calcification of muscle in a subject. The plasmin(ogen) may be natural plasmin(ogen) or synthetic plasmin, such as recombinant plasmin. In certain embodiments, a combination of a downregulator of one or more plasmin inhibitor and plasmin(ogen) may be administered to individuals having a disease or condition which reduces or eliminates natural production of plasmin(ogen) and/or increases clearance of plasmin(ogen) from the body.

In some embodiments, the methods disclosed herein also include reducing or stopping administration of antifibrinolytics following severe injury. In contrast to recent suggestions that antifibrinolytic dosing in trauma and surgical patients be extended as an extra precaution to prevent hemorrhage, the instant inventors have discovered that prolonged administration of an antifibrinolytic impairs plasmin(ogen) function and promotes soft tissue calcification. Thus, in one embodiment, the methods disclosed herein include reducing or stopping antifibrinolytic dosing following trauma and/or surgery in combination with administration of plasmin(ogen) and/or a downregulator of one or more plasmin inhibitor. For example, in another embodiment, the administration of an antifibrinolytic is stopped within three (3) days following trauma and/or surgery, while the plasmin(ogen) and/or the downregulator of one or more plasmin inhibitor is administered before, at the time of, or subsequent to the injury. As will be appreciated by those skilled in the art, stopping administration of the antifibrinolytic is not limited to within three (3) days following injury, and may include any other suitable time period to prevent hemorrhage without impeding healing. Other suitable time periods include, but are not limited to, within five (5) days following injury, within four (4) days following injury, within three (3) days following injury, within two (2) days following injury, within 24 hours following injury, within 18 hours following injury, within 15 hours following injury, within 12 hours following injury, within 10 hours following injury, within 5 hours following injury, or any range or sub-range thereof.

The presently-disclosed subject matter is further illustrated by the following specific but non-limiting examples. The following examples may include compilations of data that are representative of data gathered at various times during the course of development and experimentation related to the presently disclosed subject matter.

EXAMPLES

Example 1

The molecular mechanisms that protect muscle from dystrophic calcification after injury are unclear. A finding common to severe traumatic injuries associated with HO is hypofibrinolysis. Plasminogen, activated to plasmin, the primary fibrinolytic protease, supports numerous biological functions in addition to fibrinolysis and is seminal to virtually all tissue repair. The instant inventors recently discovered that following fracture, plasminogen deficiency not only imposes major deficits in fracture regeneration, but also induces HO in adjacent musculature. Recognizing that plasminogen promotes osteogenesis in fracture repair, it was considered unlikely that a plasminogen deficiency would reciprocally promote osteogenesis in muscle. Alternatively, it was hypothesized that plasminogen regulates dystrophic calcification in muscle following injury. In support of this hypothesis, plasminogen deficiency has been anecdotally associated with dystrophic calcification of the liver after injury. To test this hypothesis, the instant inventors explored whether genetically or pharmacologically manipulating plasmin(ogen) activity affect HO after muscle injury.

Materials and Methods

Animal Models and In Vivo Pharmacological Manipulation

All animal procedures in this protocol were approved by the Institutional Animal Care and Use Committee.

Cardiotoxin-Induced Muscle Injury Model: Skeletal muscle injury was induced by an intramuscular injection of 40 μL of 10 nM Cardiotoxin (CTX, Accurate Chemical and Scientific Corp; Westbury, NY) in the posterior compartments of the lower extremities of male C57/B6 mice. Briefly, following anesthetization with Isoflurane, CTX was injected into the lateral aspect of the posterior compartment using a 28.5 G, 0.5 cc insulin syringe. The CTX induces massive local myocyte depolarization, leading to myocyte death. However, muscle resident stem cells are unaffected by the CTX, thereby allowing for muscle regeneration following injury.

Burn-Induced Injury Model: All burn studies were conducted in 6-week-old male C57/B6 mice, weighing 20-25 g as previously described(69). All mice were anesthetized using 2.5% Isoflourane. Prior to receiving a burn injury, mice assigned to the injury group received a CTX injection to the posterior compartments of lower extremities as previously described. All mice, then receive a subcutaneous injection of 0.3-mg/mL buprenorphine at 0.5-mg/kg 30 minutes prior to the burn procedure to ensure adequate analgesia post burn procedure. Dorsal hair of the mouse was shaved and 1 ml of saline was injected subcutaneously posterior to the spine to protect the underlying spinal column from thermal injury. The mouse was then placed in a heat-resistant template with the exposed dorsum positioned in the cutout of the template. The template was then partially submerged in a 100° C. water bath for 10 seconds to create a full thickness cutaneous burn covering approximately 30% of the body surface area. The mouse was then dried and given 2 ml of intraperitoneal fluid resuscitation with lactated Ringer's solution.

Crush Injury Model: To begin, mice were anesthetized with Isofluorane. Once appropriately sedated, a sterile incision was made on the posterior hindlimb of a mouse in the prone position under. The gastrocnemius was separated from underlying tissue using blunt dissection beginning anterior to the Achilles tendon and proceeding superiorly along the anterior gastrocnemius. Once the muscle had been freed, a needle driver was clamped around the muscle at its maximum diameter in the axial plane for 30 seconds and released. Skin was closed with 4-0 monofilament suture.

Antisense Oligonucleotide (ASO) Injections: All ASOs used in this study were developed in collaboration with Ionis Pharmaceuticals (Carlsbad, CA). Plasminogen (Plg) (AGT-GATGGTCTATTGTCACA), alpha 2-antiplasmin (α2AP) (CACTGGTGATGGTCCTTCCG), Fibrinogen (Fbg) (GCTTTGATCAGTTCTTTGGC), and control ASOs (CCTTCCCTGAAGGTTCCTCC) were all subcutaneously dosed in the abdomen weekly beginning two weeks prior to injury and continuing through the term of the study. All ASO treatments were dosed at 330 mg/kg/week. Unless noted in the figure.

The ASOs used in this investigation were chemically modified with a phosphorothioate backbone, 2' O methoxyethyl on the wings with a central deoxynucleotide gap. ASOs targeted hepatic translation of their targeted protein. ASOs were synthesized using an Applied Biosystems 380B automated DNA synthesizer (Applied Biosystems) and purified as described previously. In order to identify the most potent fibrinogen ASOs for animal testing, ASOs were designed and tested in primary mouse hepatocytes for their ability to suppress mRNA levels of the respective targets.

Non-Hydrolysable Synthetic Pyrophosphate Treatment: Zoledronic acid (200 ug/kg) was administered via subcutaneous injection weekly beginning two weeks prior to injury and continuing for the duration of the study.

Output Analysis and Quantification of Heterotopic Ossification

Radiographic Imaging: Radiographic imaging was performed as previously described. Briefly, following adequate anesthesia, digital radiographs (Faxitron Tucson, AZ) were collected at an exposure of 4 seconds at 35 kV. Mice were placed in the prone position with hips in abduction, allowing for external rotation of the leg placing the tibia in a reproducible lateral position.

Radiographic Analysis and Quantification of HO: Quantification was performed as described. Seven days post injury (DPI), digital radiographs were obtained as outlined above. These images underwent post-image standardization and were quantified with the previously validated heterotopic ossification scoring scale. The heterotopic ossification scoring scale is an ordinal scale (0-4) of varying degrees of HO formation, based on the percentage of the lower extremity soft tissue silhouette containing radiographically evident calcification. A blinded reviewer assessed all scores (a score of 1=0-24%, a score of 2=25%-49%, a score of 3=50%-74%, and a score of 4=>75% of the lower extremity containing radiographically evident HO).

Ex vivo μCT Imaging and Quantification of HO: μCT mages were acquired (μCT40, Scanco Medical AG, Bassersdorf, Switzerland) following specimen harvest of injured hindlimbs at 55 kVp, 145 uA, 200 ms integration, 500 projections per 180° rotation, with a 20 μm isotropic voxel size. After reconstruction, a volume of interest (VOI) was selected comprising the mineralization within the posterior compartment of the lower extremity. The mineralized tissue within the VOI was segmented from soft tissue using a threshold of 132 per thousand, a Gaussian noise filter of 0.2, and support of 1. Mineral volume was then calculated using the Scanco evaluation software.

Histological Analysis and Quantification: Injured hind limbs were fixed in 4% paraformaldehyde overnight. Samples not requiring the observation of mineral deposition were then decalcified in 0.5 M EDTA (pH 8.0) for approximately 5 days prior to processing. All samples were processed in graded series of ethanol, cleared, and embedded in paraffin prior to sectioning. 6 μm sections were cut and stained as described below.

Histological Staining

Hematoxylin and Eosin (H&E): Deparaffinized sections were stained in Gills 3 hematoxylin solution for 5 minutes. Slides were then rinsed in tap water for 10 minutes followed by eosin staining. Finally, slides were dehydrated and cleared in xylene before mounting with Permount.

Safranin-O/Fast Green Stains (Safranin-O): Deparaffinized sections were rehydrated and placed in freshly filtered working Weigert's hematoxylin for 10 minutes. Slides were then immediately washed in running tap water for 10 minutes followed by staining with 0.1% Fast green solution for 5 minutes. Slides were then rinsed quickly in 1% acetic acid for no more than 10-15 seconds and then placed in 0.1% Safranin O solution for 5 minutes. Finally, slides were dehydrated through two changes of 95% ETOH and 100% EtOH for 3 minutes each and cleared in two changes of xylene for 5 minutes. Slides were then coverslipped with Permount.

TRAP staining: Deparaffinized sections were stained in a fast Garnet GBC, napthol—AS-Bi Phosphate solution containing acetate and tartrate for 10 minutes. Slides were then placed in deionized water to stop the reaction and coverslipped using aqueous mounting medium.

Von Kossa staining: Deparaffinized sections were stained in 1% aqueous silver nitrate solution for 60 mins under a UV lamp. Sections were then washed in distilled water for 1 minute followed by fast green staining for 10 minutes. Finally, slides were dehydrated and cleared in xylene before cover slipping with Permount.

Whole Body Alizarin Red and Alcian Blue staining: Following dissection and removal of viscera, mice were placed in 100% ETOH and allowed to fix for 24 hours. Mice were then placed in an Alcian Blue solution of 95% ETOH and 20% glacial acetic acid for 24 hours. Mice then underwent 4 washes of 95% ETOH and were place in 2% solution of KOH for 24 hours. Mice were then washed twice in 95% ETOH and placed in an Alizarin Red solution for 24 hours. Finally, mice were placed in a 20% glycerol 1% KOH solution to remove excess staining and clear unstained tissue prior to imaging.

Immunohistochemical Staining: Deparaffinized and rehydrated samples were processed for antigen retrieval by heating for 2 minutes in 0.1M citric acid and 0.1M sodium citrate. Subsequently, the endogenous peroxides were quenched with the 3% $H_2O_2$ for 15 minutes. Slides were then gently washed with phosphate buffered saline (5 min×3 times), and then blocked for 30 minutes using the Blocking Solution (TSA kit Perkin Elmer; Waltham, MA). Slides were then immunostained using a rat anti mouse F4/80 antibody (MCA497 AbD Serptec; Raleigh, NC) at 1:100 dilution in the provided blocking solution overnight at 4° C. Slides were then washed with TNT wash buffer (5 min×3 times). A biotin conjugated goat anti-rat secondary antibody (BD Pharmigen, 559286 BD Bioscience; San Jose, CA) was diluted 1:100 with blocking buffer and incubated with the slides for 60 minutes. Following TSA signal amplification, the Dako Envision+ HRP/DAB System (Catalog #K4007, Dako; Carpinteria, CA) was used to visualize antibody staining. Slides were counterstained with Mayer's hematoxylin and cover slipped with an aqueous mounting medium.

Immunofluorescent Staining: Slides were deparaffinized, rehydrated, and processed for antigen retrieval as previously described. Slides were then gently washed with tris-buffered saline (TBS) and blocked with a 5% BSA solution containing 10% goat serum. Following blocking, slides were immunostained with a rabbit anti-mouse Fibrin(ogen) (1:1000) antibody overnight at 4° C. Slides were then washed with TBS and incubated with 10 μg/mL of Alexa Fluor 647-labeled anti-rabbit antibody (Life Technologies 792514, Grand Island, NY) in blocking buffer for 1 hour at room temperature. Finally, slides were counterstained with DAPI and coverslipped using an aqueous mounting solution (PolySciences Warrington, PA).

Histological Quantification

Measurement of regenerating and degenerating muscle by H&E: Muscle regeneration and degeneration was assessed by light microscopy using a 200× objective (Axio imager al, ZEISS; Oberkochen, Germany). Skeletal muscle regeneration was evaluated by counting the number of centrally nucleated muscle fibers present within each individual 200× field. Skeletal muscle degeneration was evaluated by counting necrotic sarcomeres (identified by hypereosinophilic hyaline cytoplasm and absence of nuclei). Counts of regenerating and degenerating myocytes were expressed as a percentage of total muscle fibers (including all necrotic, regenerating, and uninjured sarcomeres within a 200× magnified field). A minimum of 2 mice per group were analyzed.

Histologic quantitation of $Plg^{+/-}$ mice 28 days post Injury: The presence of bone formation (identified by the presence of woven bone) and the necrotic muscle (identified by the presence of hypereosinophilic, hyalinized cytoplasm and absence of nuclei) were determined by light microscopy of H&E stained muscle at 200× magnification. Sides were scored in a binary method for either the presence or absence of bone and narcotic muscle. The ratio of the positive samples to the ratio of negative samples was then expressed in a table.

Fibrin(ogen) Deposition Analysis by Immunofluorescent Staining: All the slides were assessed under the fluorescent microscope and images were taken. Each section was exposed for 2 seconds using Cy5 filter at 200× magnification. Images were obtained and the fibrin(ogen) area was quantified using ImageJ (nih.gov). Results were expressed as number of fluorescent pixels per image.

Macrophage Migration Measurement by Immunohistochemical Staining: The number of anti-F4/80-positive cells were quantified in 200× magnification using quantified using ImageJ (nih.gov). Each treatment group consisted of 4 mice.

The individual fields of injured skeletal muscle were analyzed and results were averaged per experimental group.

Quantification of Plasminogen and Plasmin Activity

Plasminogen Level: Circulating plasminogen levels were determined with a commercial sandwich ELISA (Molecular Innovations; Novi, MI) from both murine citrated plasma obtained by cardiac puncture at the time of sacrifice, and burn patient plasma samples obtained one and three days following burn injury.

Plasmin Activity: Plasmin activity was analyzed in citrated plasma from both murine and human burn patients. Plasma was diluted (1:230.9) in a 50 mM HEPES, 125 mM sodium chloride buffer (Sigma Aldrich; St. Louis, MO). Plasmin activity was measured using a florescent substrate for plasmin (AS-24133, Anaspec; Fremont, CA) on a microplate reader (Synergy 2, BioTek Winooski, VT). Percent Activity was reported as the ratio of sample activity to control activity.

Clinical Assessment of Burns: Patient burns were quantified and stratified using Total Body Surface Area (TBSA) and APACHE II Scoring System. APACHE II is a validated scoring method in which an increasing score correlates with risk of hospital death and prognosis following burn injury (74). TBSA was calculated in accordance with the Lund and Browder Chart.

Statistical Analysis

Soft Tissue Calcification Score: HO score statistical comparisons between groups were conducted using the Mann-Whitney rank test. (*=P<0.05 and **=P<0.001). To further strengthen the analysis a proportional odds model with random effects was also performed using SPSS. This test takes into account intra-individual correlation between paired samples (right and left legs) of a single mouse. However, this model cannot be applied when the number of mice in a group is low or when ordinal scores are relatively homogeneous and distinct within the groups. Thus, the results from the Mann-Whitney rank test are reported for all figures and the proportional odds model is reported when statistically appropriate. All Mann-Whitney rank test calculations were performed using Graphpad Prism version 6 (La Jolla, CA).

Histological Quantification: Statistical significance was calculated using a Mann-Whitney Rank test. P values and number were denoted within the figure legend. Quantitation of bone formation and muscle necrosis 28 DPI was analyzed using a two tailed Fisher's exact test. A P value of less than 0.05 was considered significant.

Results

Figure 1A:
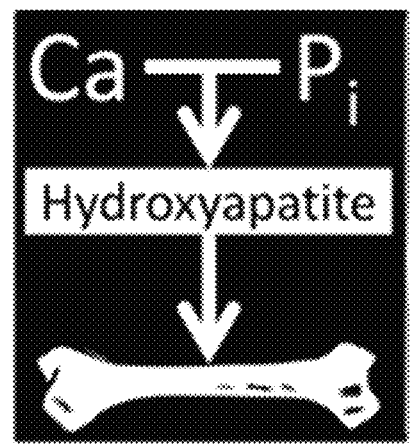
FIGS. 1A-B show images illustrating ossification and calcification. A) All multicellular organisms catalyze the aggregation of calcium and phosphate into crystals, most notably hydroxyapatite, which are further assembled into complex structures such as bone. This process also occurs aberrantly within injured soft tissue, referred to as dystrophic calcification, leading to chronic inflammation and tissue dysfunction. This proposal addresses key knowledge gaps in the pathophysiology of dystrophic calcification, specifically in the process of forming heterotopic ossification (HO) within injured skeletal muscle. B) Diseases of soft tissue calcification.
Figure 1B:
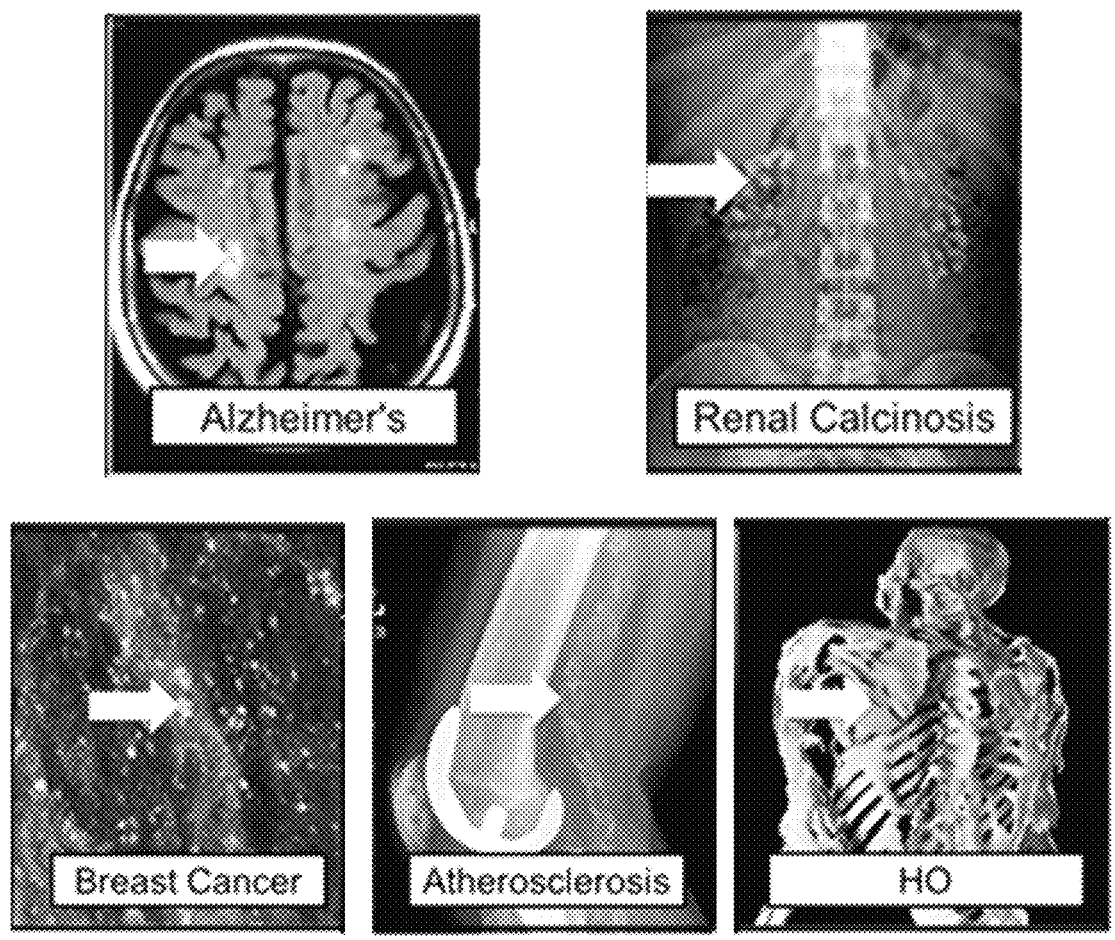
Figure 2:
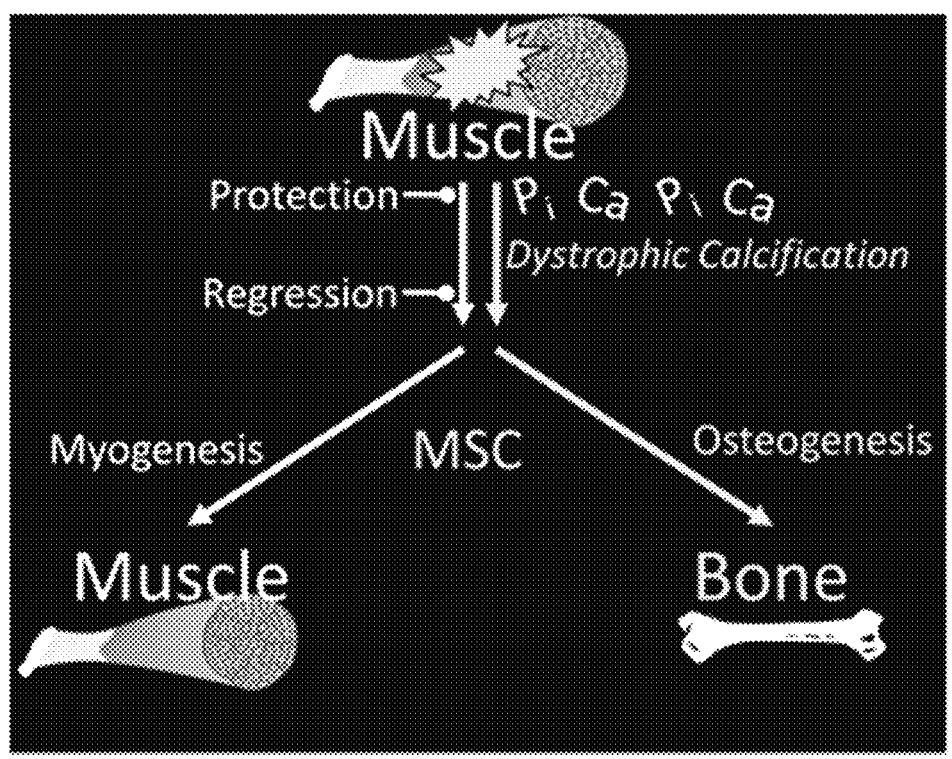
FIG. 2 shows a schematic illustrating that following injury muscle typically undergoes myogenesis by resident muscle stem cells (MSC). If the mechanisms that protect against the formation of dystrophic calcification or those which promote the regression of dystrophic calcification are insufficient, muscle either develops chronic inflammatory dystrophic calcification or undergoes osteogenesis and forms bone within muscle referred to as heterotopic ossification (HO).
Figure 3:
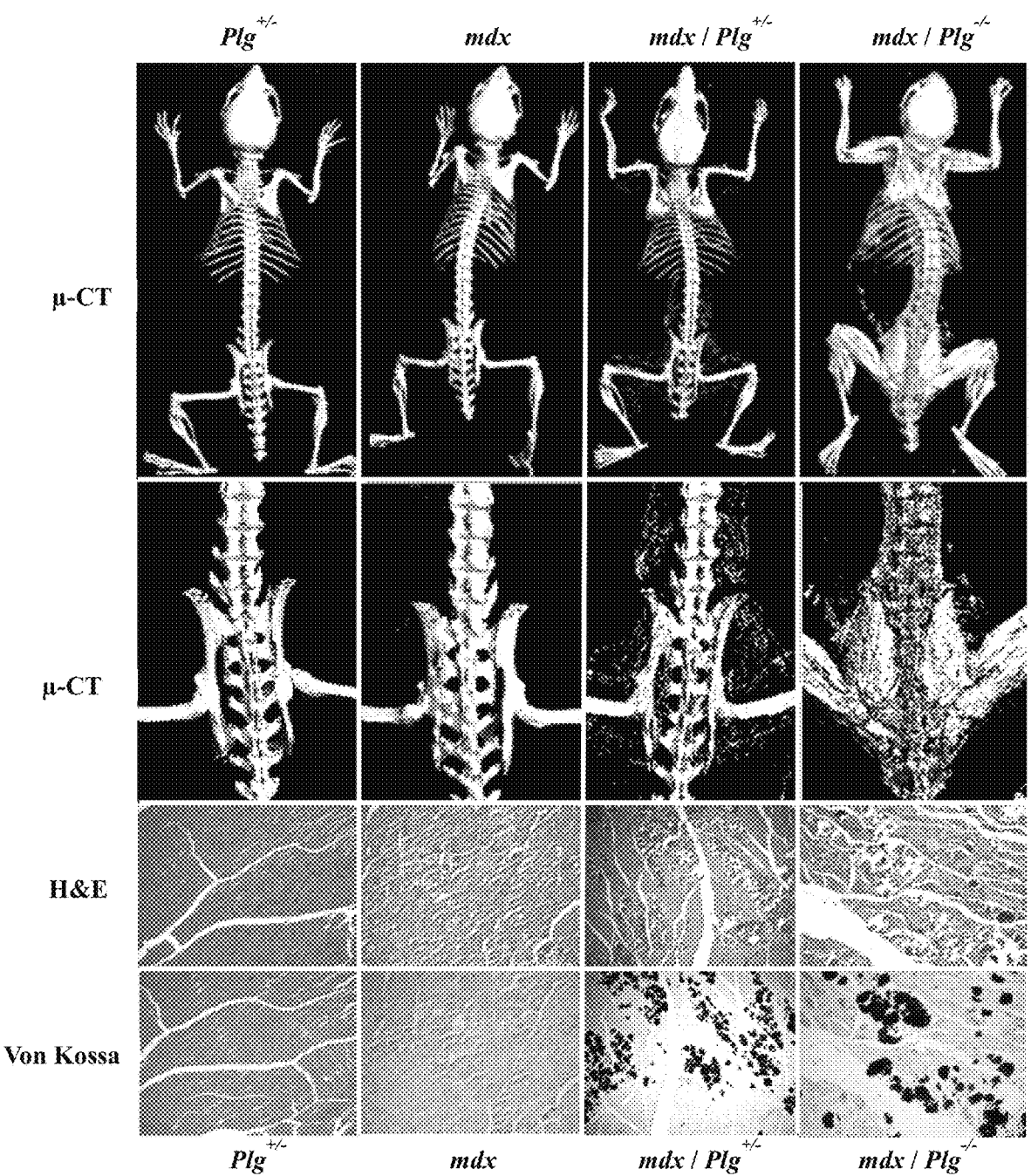
FIG. 3 shows images illustrating continuous muscle injury in the setting of plasminogen deficiency resulting in soft tissue calcification. Full body μCT reconstruction of $Plg^{+/-}$, mdx, mdx/$Plg^{+/-}$ and mdx/$Plg^{-/-}$ mice with focused magnification of paraspinal and pelvic musculature. $Plg^{+/-}$ mice without muscle injury showed no apparent calcification within skeletal muscle. Similarly, plasminogen-competent, mdx mice suffering continuous, chronic muscle injury also showed no muscle calcification. In contrast, mdx mice with either a partial (mdx/$Plg^{+/-}$) or complete plasminogen deficiency (mdx/$Plg^{-/-}$) showed calcification within all major skeletal muscle groups. H&E of $Plg^{+/-}$ mice revealed unremarkable, uninjured sarcomeres with peripherally located nuclei, whereas mdx, mdx/$Plg^{+/-}$, and mdx/$Plg^{+/-}$ mice demonstrated interspersed necrotic (glossy, hypereosinophilic with absent nuclei) and regenerating (centrally located nuclei) sarcomeres. Von Kossa stain demonstrates no calcifications in $Plg^{+/-}$ and mdx mice, but marked dystrophic calcifications within necrotic sarcomeres of mdx/$Plg^{+/-}$ and mdx/$Plg^{-/-}$ mice.

Plasminogen Prevents Soft Tissue Calcification in Muscle Genetically Predisposed to Injury To determine whether loss of the plasminogen zymogen or plasmin protease activity establishes an osteoinductive microenvironment in the context of muscle injury, heterozygous ($Plg^{+/-}$) or homozygous ($Plg^{-/-}$) plasminogen deficiency was genetically imposed on Duchenne muscular dystrophy (mdx) mice. Mdx mice sustain continuous muscle injury due to the lack of the muscle cytoskeletal protein, dystrophin. μCT analysis of mice with singular deficiencies in either plasminogen or dystrophin demonstrated no soft tissue calcification. In contrast, soft tissue calcification was observed in skeletal muscle of mice with combined dystrophin/plasminogen deficiency ($mdx/Plg^{+/-}$ and $mdx/Plg^{-/-}$ mice) (FIGS. 3 and 11A-B). The degree of soft tissue calcification appeared proportional to the level of genetic plasminogen deficiency. These findings indicate that deficiency in plasmin(ogen), either the plasminogen zymogen or plasmin protease, is sufficient to cause soft tissue calcification in the setting of chronic muscle injury—even without associated bone fracture or major trauma. Histologic analysis determined the specific type of soft tissue calcification observed in $mdxPlg^{+/-}$ and $mdx/Plg^{-/-}$ mice to be dystrophic calcification of necrotic sarcomeres (FIG. 3). These data complement and extend previous findings that soft tissue calcification is sporadically observed in mdx mice lacking urokinase-type plasminogen activator and imply that plasmin activity, not the plasminogen zymogen, is key in preventing soft tissue calcification in muscle.

Plasminogen Prevents Soft Tissue Calcification in Muscle After Traumatic Injury

Figure 4A:
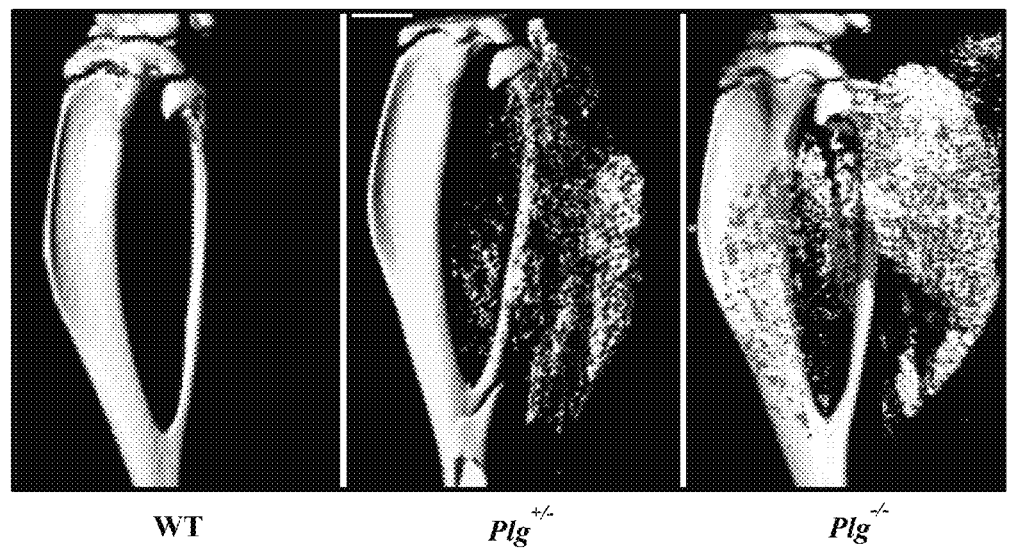
FIGS. 4A-E show graphs and images illustrating continuous and acute plasminogen deficiency resulting in muscle calcification after acute muscle injury. (A) μCT reconstructions of the lower leg of WT, $Plg^{+/-}$ and $Plg^{-/-}$ mice 7 days following CTX injury; note the moderate to severe muscle calcification in mice with plasminogen deficits. (B) Plasminogen ELISA on murine plasma confirmed reduced circulating levels according to plasminogen genotype. (N≥8;**P<0.001; Mann-Whitney test vs. WT) (C) Pharmacologic reduction of plasminogen in WT mice with a plasminogen ASO prior to injury led to a $Plg^{Low}$ phenotype and markedly more muscle calcification 7 days post injury (DPI) than control$^{ASO}$-treated WT mice, indicating that plasminogen prevents muscle calcification independent of the method of plasminogen reduction. (D) Plasminogen ELISA on murine plasma confirmed reduced circulating levels with increasing plasminogen ASO dosing (N≥4;*P<0.05; Mann-Whitney test vs. Control ASO) (E) The extent of soft tissue calcification in these models was scored using plain radiographs and a semi-quantitative scoring method similar to the Brooker classification system for HO. Graphical summary of Soft Tissue Calcification Scores in various experimental cohorts at 7 DPI using this semi-quantitative method showed increasing calcification scores, as measured by the STiCSS, with reduced circulating plasminogen levels. Medians and interquartile ranges are denoted (N≥9;**P<0.001; Mann-Whitney test vs. WT).
Figure 4B:
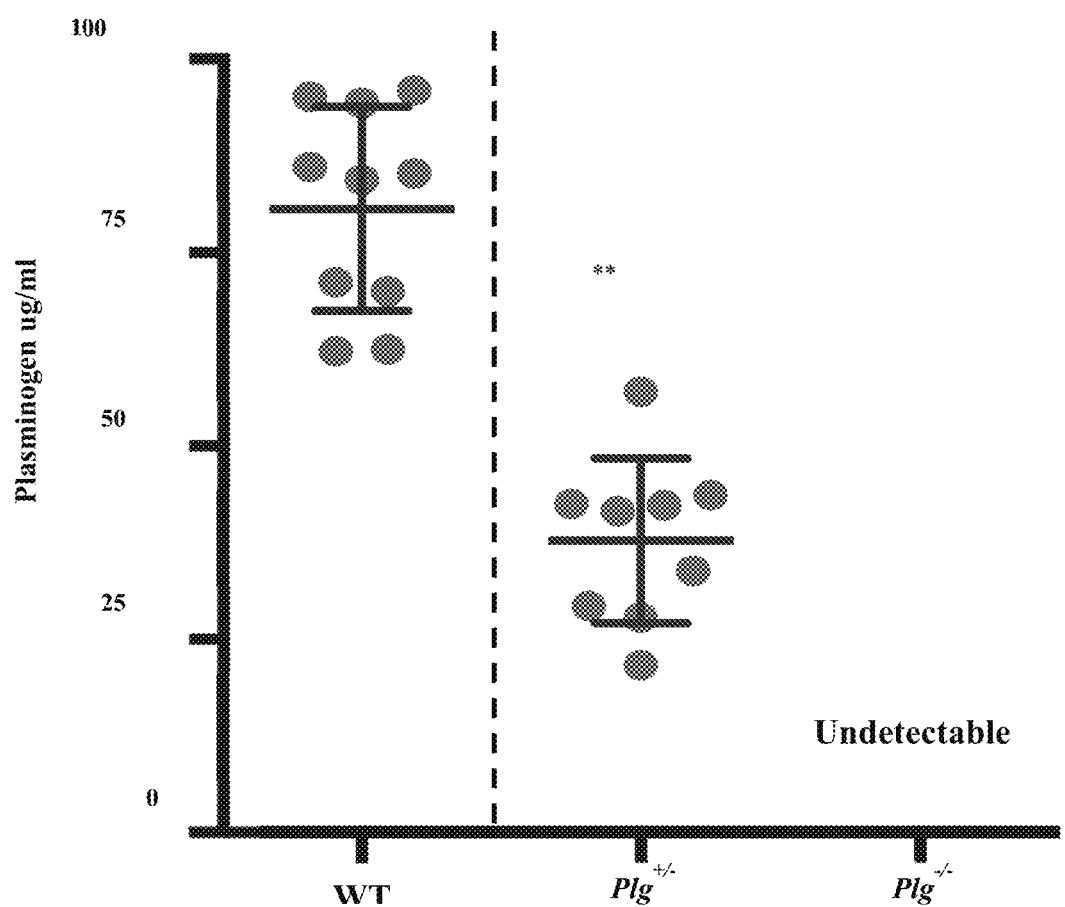
Figure 4C:
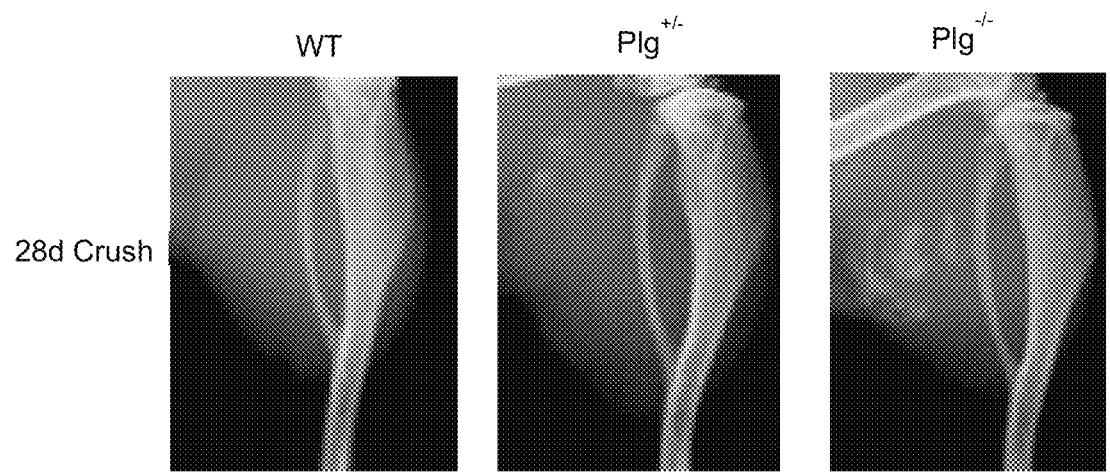

Skeletal muscle injury in $mdx/Plg^{+/-}$ mice is continuous but temporally and spatially heterogeneous, complicating assessment of soft tissue calcification in the muscles of these mice. Therefore, we evaluated the impact of congenital plasminogen deficiency on localized, acute muscle injury induced by cardiotoxin (CTX) injection to specifically target the site of myocyte damage. As in the continuous muscle injury model, acute muscle injury in the context of plasminogen deficiency resulted in dramatic soft tissue calcification at the site of injury (FIG. 4A). Reduced circulating plasminogen levels were confirmed in genetically deficient murine models (FIG. 4B). Importantly, soft tissue calcification was not restricted to CTX-induced muscular injury, as similar findings were observed in a tissue crush injury model (FIG. 4C). Thus, congenital plasminogen deficiency combined with focal, acute muscle injury is sufficient to cause soft tissue calcification of skeletal muscle.

Figure 4D:
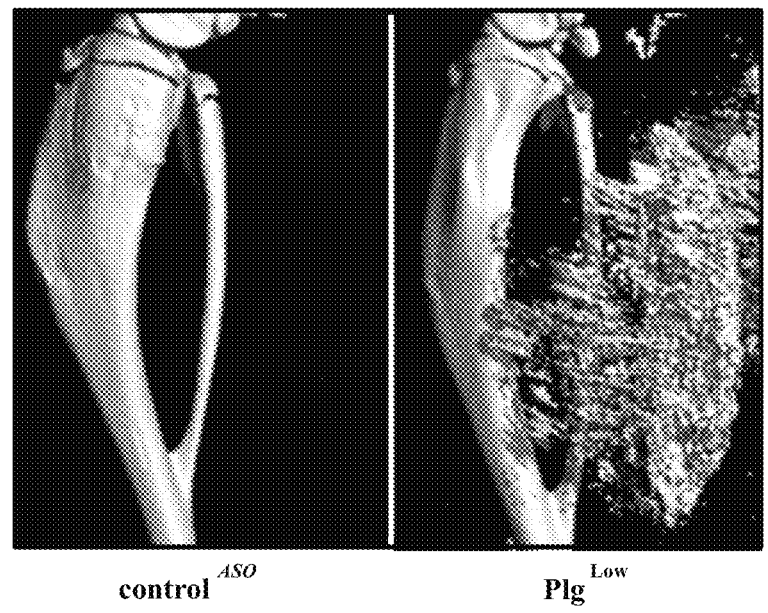
Figure 4E:
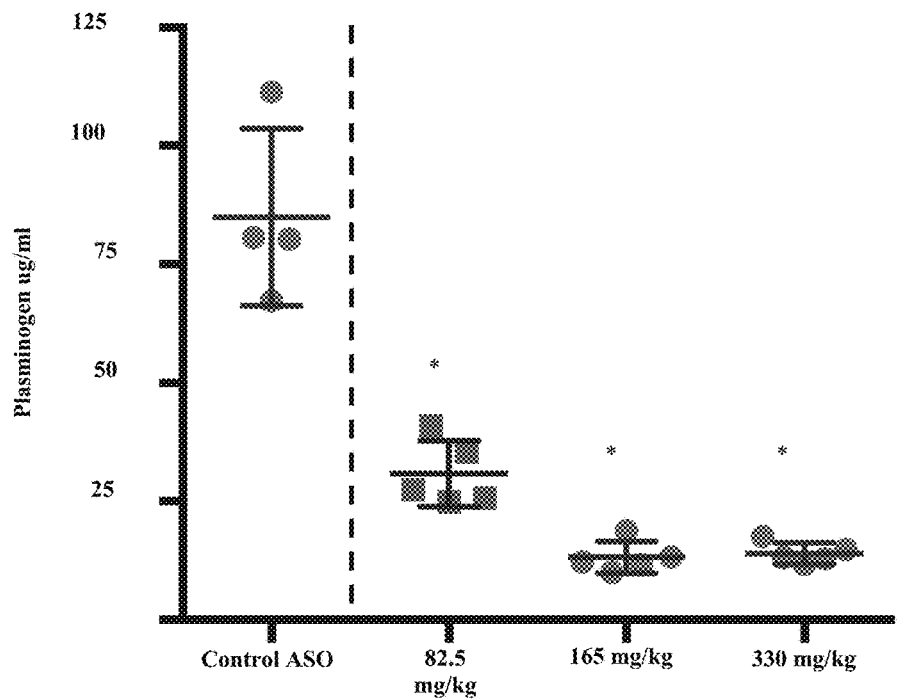
Figure 4F:
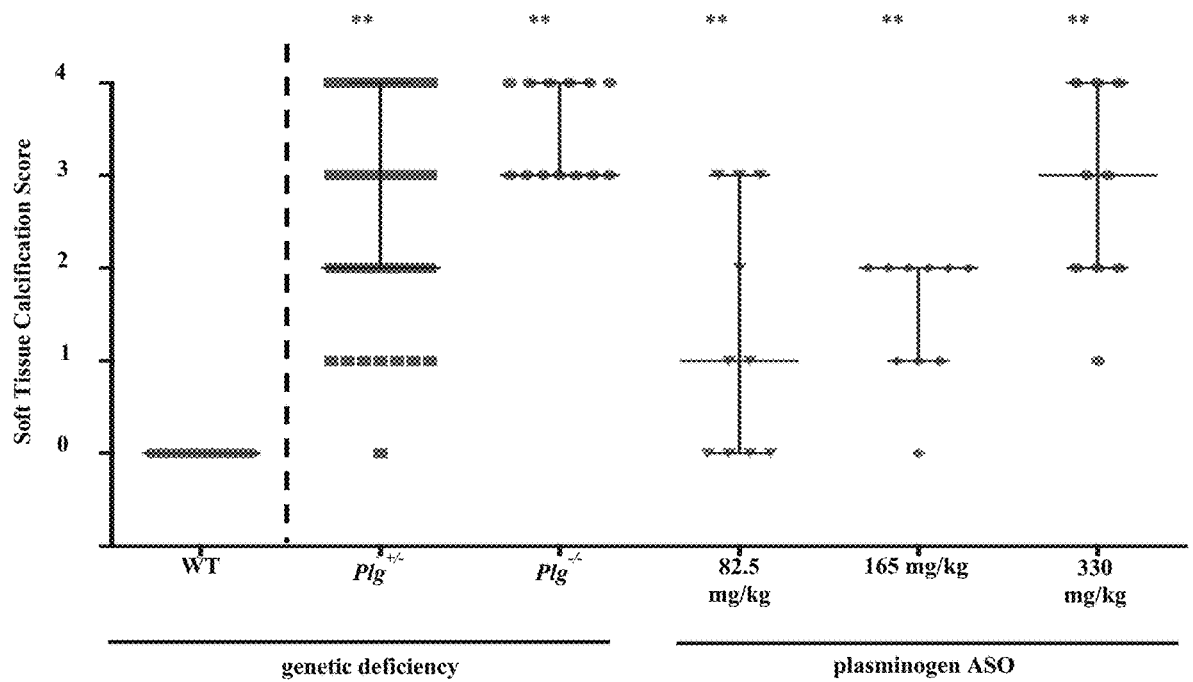

Because congenital plasminogen deficiency is associated with accelerated skeletal degeneration and impaired tissue regeneration, we next examined the impact of transient knockdown of plasminogen expression using a specific plasminogen antisense oligonucleotide "gapmer" (ASO). Wild-type mice treated with plasminogen ASO ($Plg^{Low}$) achieved a 95% transient knockdown of hepatic plasminogen mRNA when dosed prior to and during CTX injury. Following CTX-induced muscle injury, $Plg^{Low}$ mice also manifested soft tissue calcification within skeletal muscle indistinguishable from that observed in congenital plasminogen deficiency (FIG. 4D). Reduced circulating plasminogen levels were confirmed in $Plg^{Low}$ mice receiving varying plasminogen ASO doses (FIG. 4E). The severity of soft tissue calcification after injury increased with greater genetic plasminogen deficiency and higher plasminogen ASO dosing (FIG. 4F). Together these data establish that soft tissue calcification of skeletal muscle in mice with congenital plasminogen deficiency is not secondary to developmental defects and that muscle injury and hypoplasminogenemia are fundamental determinants of soft tissue calcification in skeletal muscle.

Figure 5A:
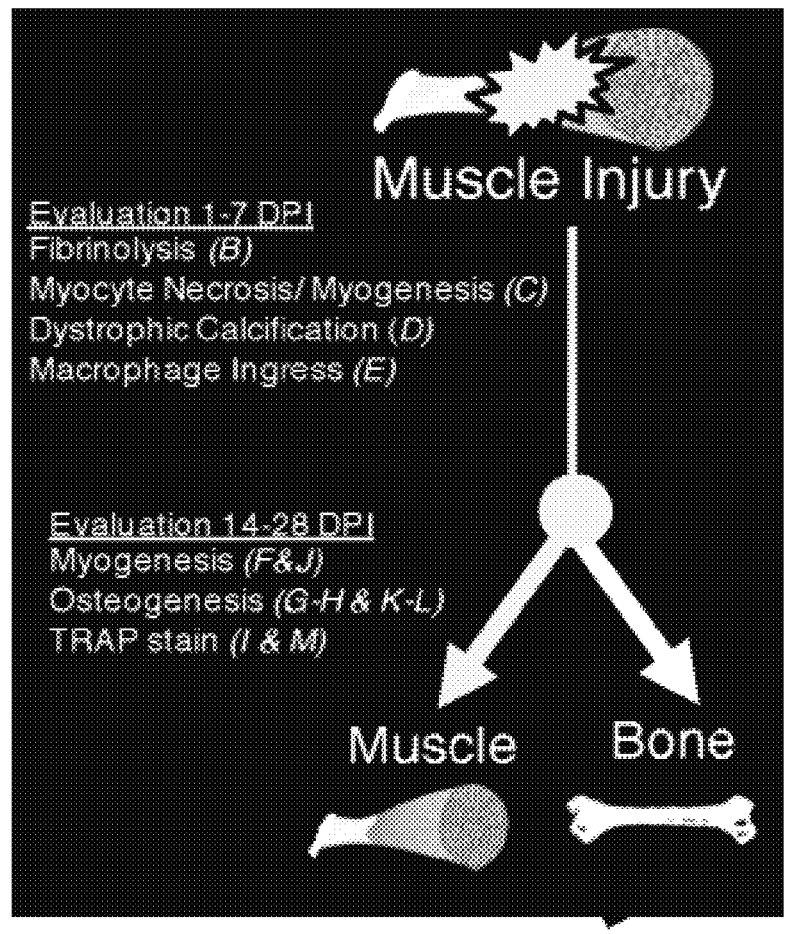
FIGS. 5A-M show images illustrating partial plasminogen deficiency and muscle injury resulting in poor muscle regeneration, persistent dystrophic calcification, diminished macrophage invasion and endochondral ossification. (A) Schematic and key of histologic analyses performed in early and late post-injury periods. (B) Fibrin(ogen) (red) clearance 7 DPI is delayed in $Plg^{+/-}$ compared to WT mice (DAPI blue counterstain). (C) H&E stain 7 DPI demonstrated more regenerating myocytes (central nuclei) in WT compared to persistent necrotic myocytes and reduced inflammatory infiltrates in $Plg^{+/-}$ mice. (D) Calcium stain (Von Kossa-black) 7 DPI highlighted exuberant dystrophic calcifications in $Plg^{+/-}$ mice relative to WT. (E) Immunohistochemical staining for F4/80 showed delayed macrophage/monocyte infiltration in $Plg^{+/-}$ mice compared to WT 3 DPI. (F-I) Endochondral ossification in $Plg^{+/-}$ mice 14 and 28 DPI. At 14 DPI, Von Kossa stains (F) revealed the presence of dystrophic calcifications and H&E stain (G) revealed persistence of necrotic myofibers and islands of chondroid matrix (confirmed by Safranin-O stain (red)(H)) intermixed with persistent dystrophic calcifications and TRAP-positive cells (purple) (I). This histologic pattern is consistent with early endochondral ossification. At 28 DPI Von Kossa (F) and H&E (G) stains showed mineralized woven bone with hematopoietic marrow and rimming osteoblasts. Safranin-O stains (H) confirmed the removal of the chondroid matrix and TRAP staining (I) revealed the presence of TRAP-positive cells surrounding woven bone. This histologic pattern is indicative of late endochondral ossification. (J-M) WT muscle regeneration 14 and 28 DPI: Von Kossa stains (J) revealed no evidence of persistent calcifications. H&E staining 9K) showed muscle regeneration (maturing myocytes with intact sarcomeric structures and central nuclei that become eccentrically located by 28 DPI). Unremarkable Safranin-O (L) and TRAP (M) stains disclosed no evidence of endochondral ossification or osteoclast-like multinucleated giant cells. (200× magnification in Figures B, D-M; 400× magnification in Figure C). (See FIGS. 12A-H for complete time course and statistical evaluation).
Figure 5B:
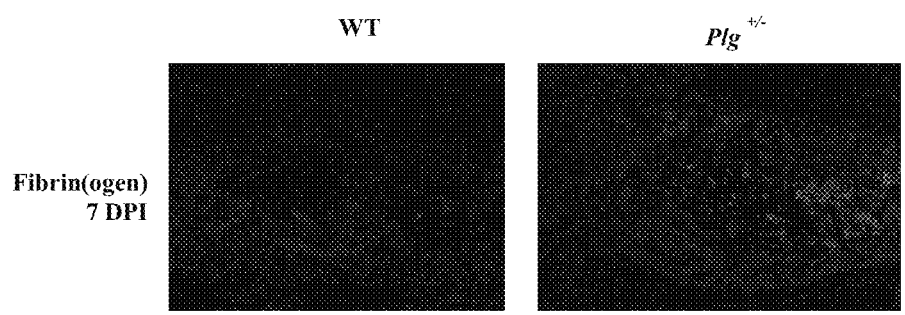
Figure 5C:
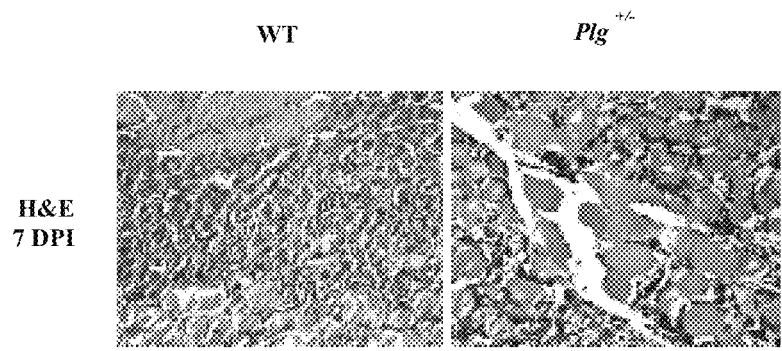
Figure 5D:
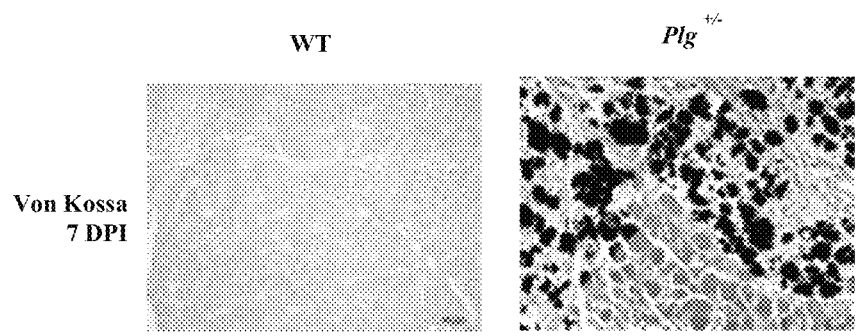
Figure 5E:
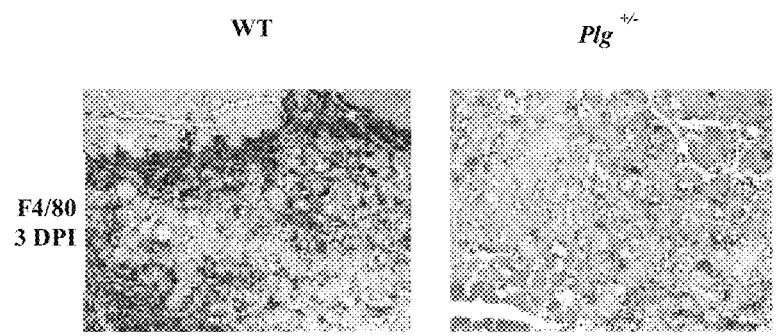
Figure 5F:
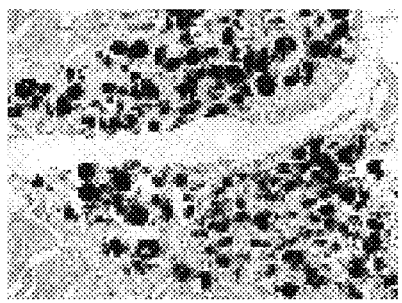
Figure 5F:
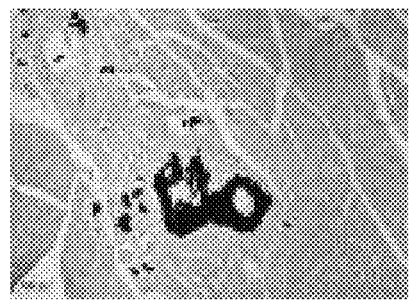
Figure 12A:
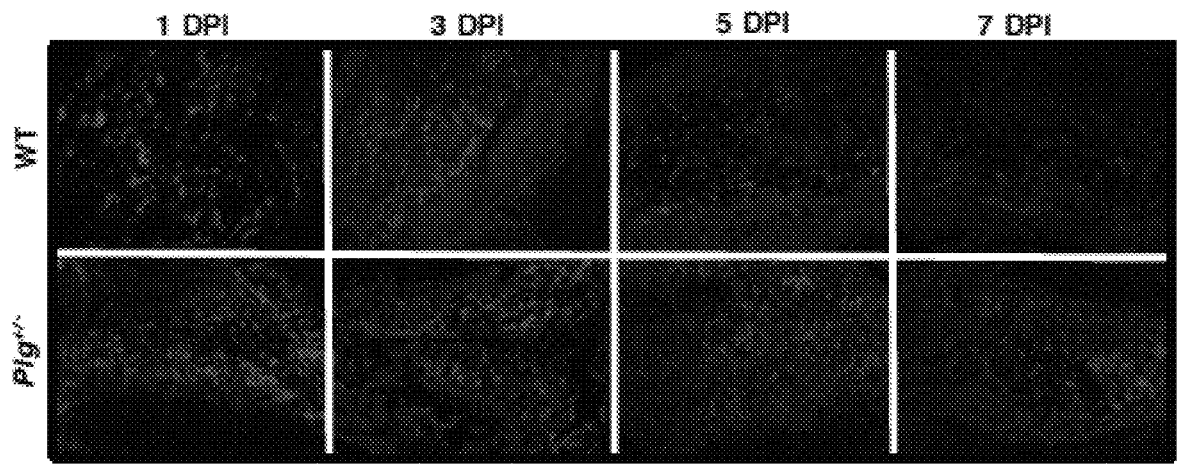
Figure 12B:
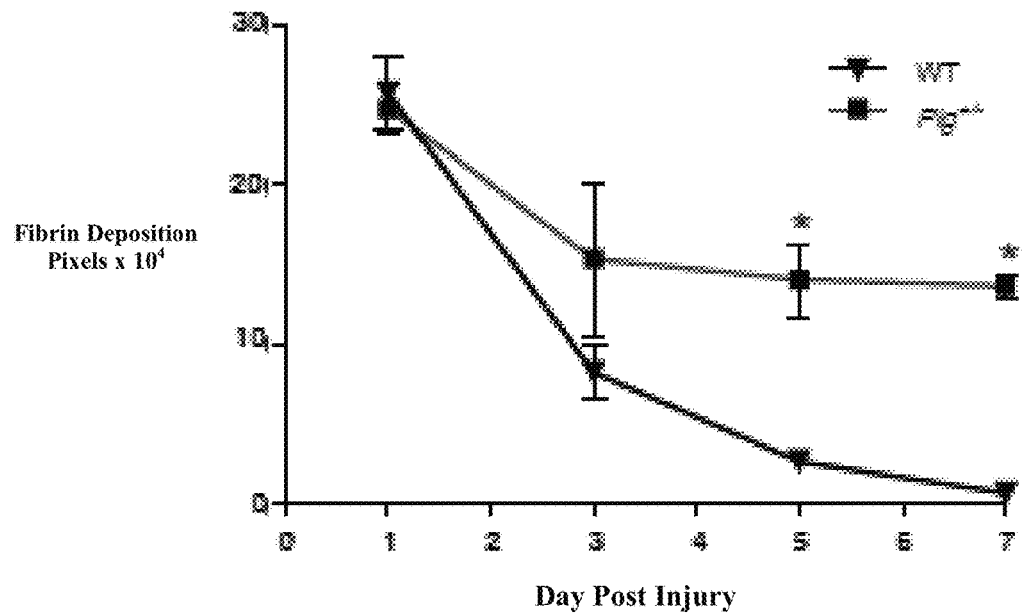
Figure 12C:
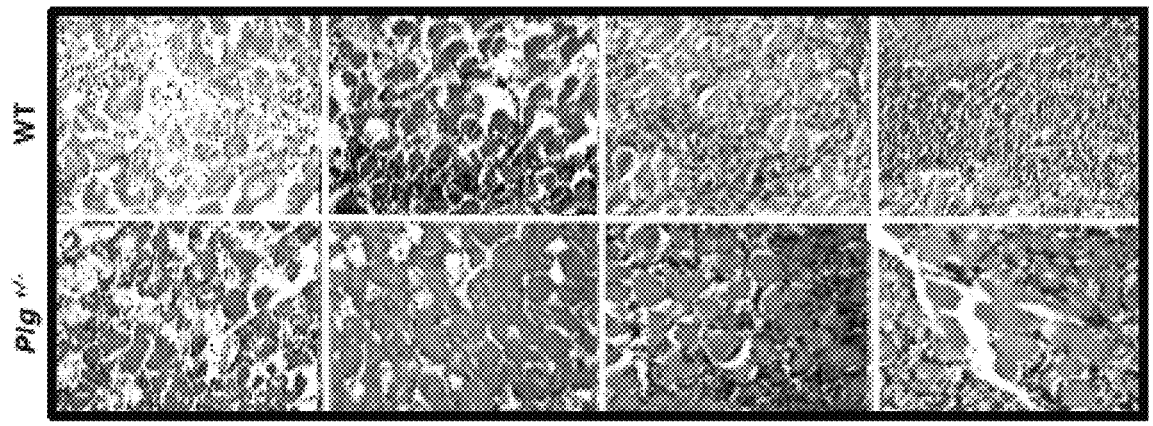
Figure 12D:
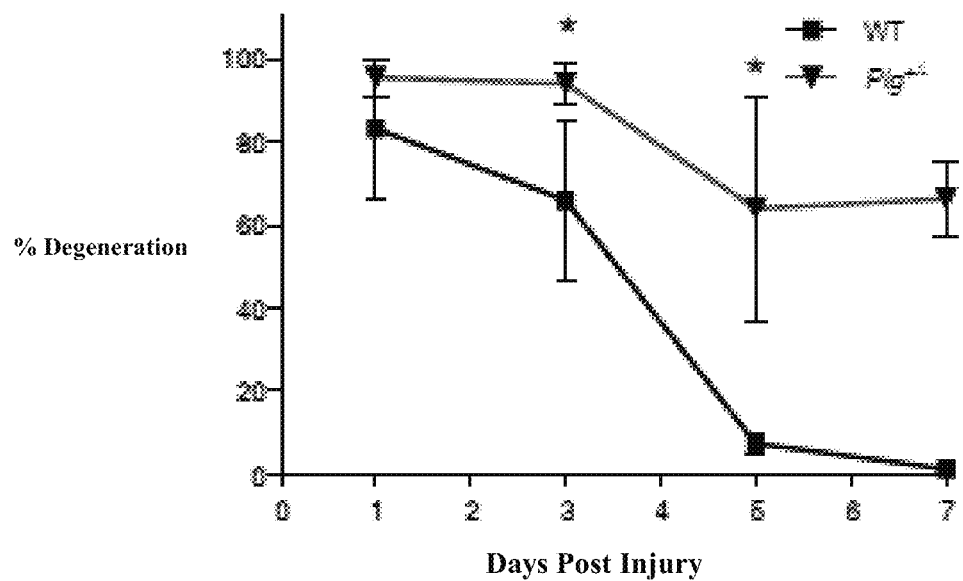
Figure 12E:
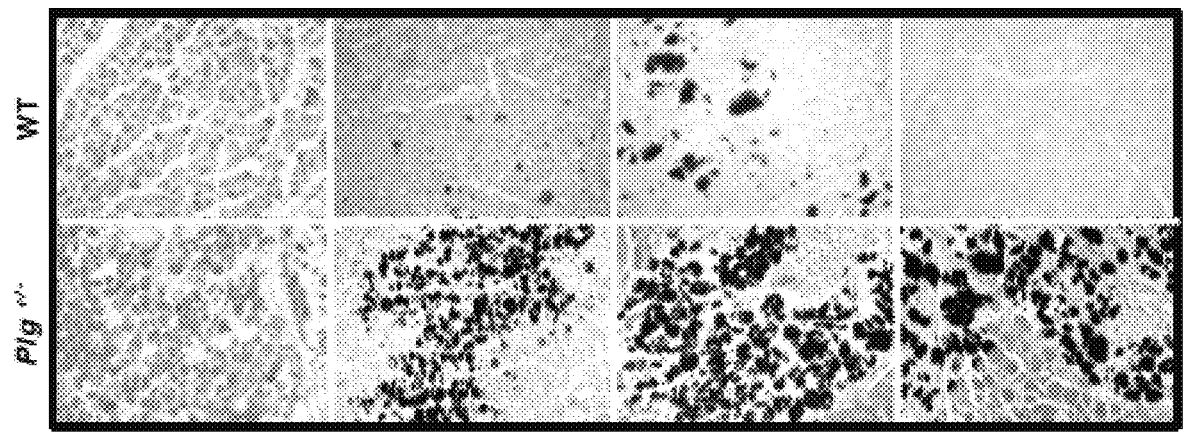
Figure 12F:
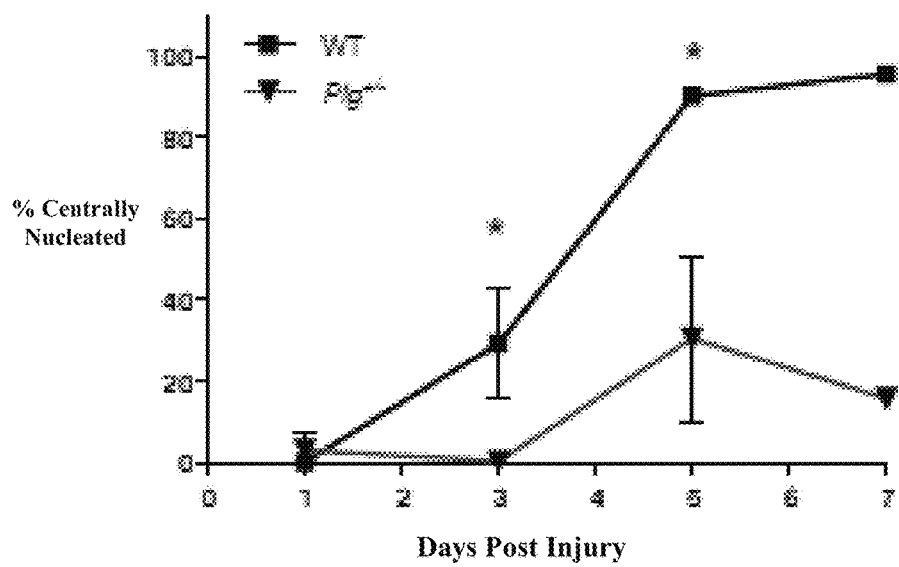
Figure 12G:
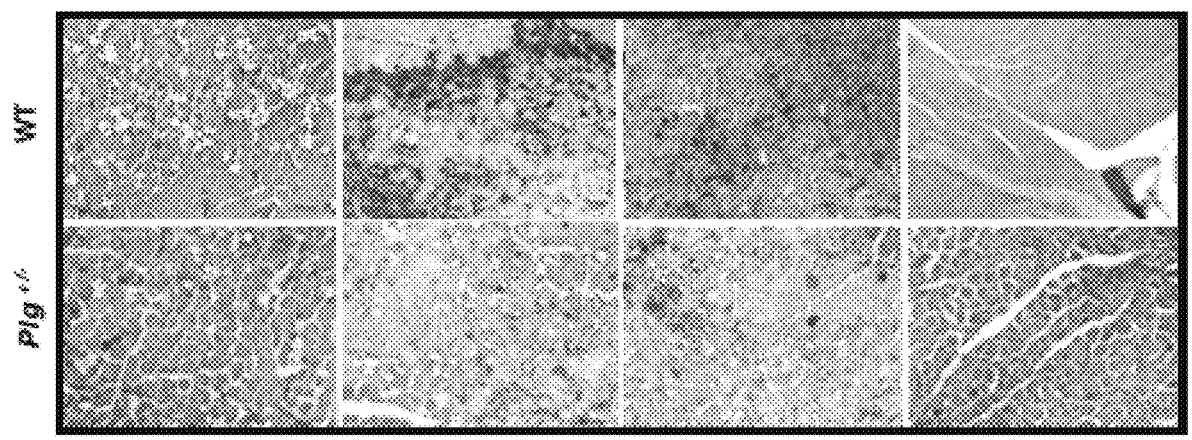
Figure 12H:
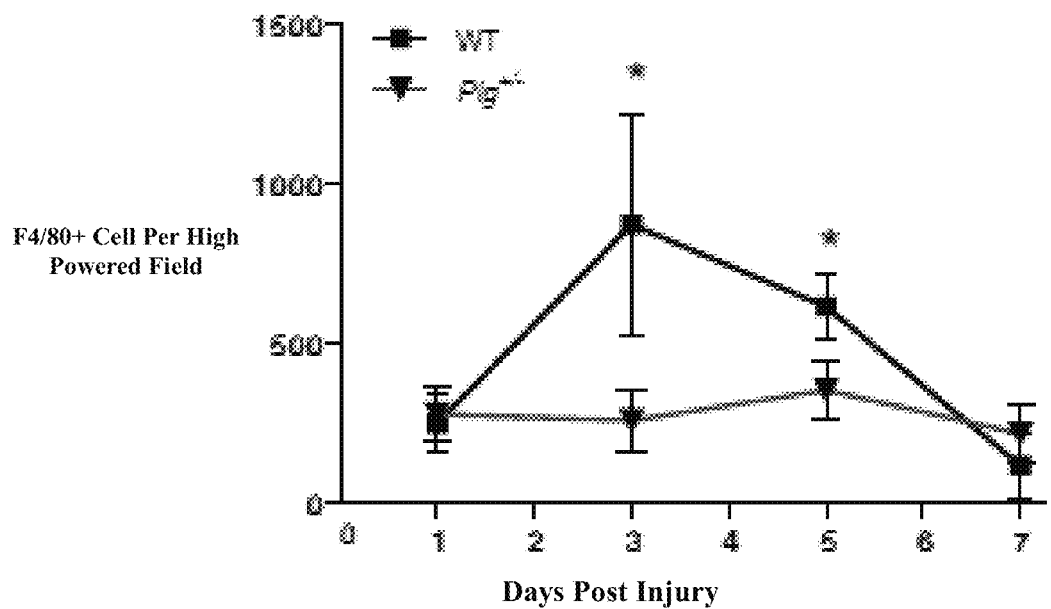

Plasminogen Deficiency and Muscle Injury are Associated with Dystrophic Calcification and Subsequent Endochondral Ossification To further define the initial pathophysiological processes that result in soft tissue calcification, we examined sites of CTX-induced muscle injury histologically over the acute (1-7 DPI) post-injury period for evidence of fibrinolysis, myocyte necrosis, myogenesis, dystrophic calcification, and macrophage infiltration (FIG. 5A). WT mice cleared fibrin deposits from the site of injury faster than Plg$^{+/-}$ mice, which supports the assumption that extravascular plasmin activity is reduced in Plg$^{+/-}$ mice (FIGS. 5B and 12A-B). In accordance with other findings that plasminogen is essential for skeletal muscle regeneration, we also observed that necrotic myocytes persisted at the injury site for at least 28 days in Plg$^{+/-}$ mice. Additionally, significantly fewer regenerating myocytes were seen in Plg$^{+/-}$ mice compared to WT mice (FIGS. 5C and 12C-E). Von Kossa stains for calcium revealed that WT mice developed a limited amount of dystrophic calcification that was completely resorbed by 5 DPI (FIGS. 5D and 12F). In contrast, exuberant dystrophic calcifications were seen in in Plg$^{+/-}$ mice up to 14 DPI (FIGS. 5D and 12F). These data indicate that plasmin(ogen) prevents crystallization and/or promotes resorption of dystrophic calcifications within necrotic muscle in the acute post injury period. Efficient fibrin clearance was temporally associated with infiltration of the injury site by monocytes/macrophages in WT mice. Conversely, both fibrin clearance and macrophage infiltration were diminished in Plg$^{+/-}$ mice. Whereas infiltration of F4/80-positive cells peaked 3 DPI in WT mice, this influx of monocyte/macrophages was not observed in injured muscles from Plg$^{+/-}$ mice (FIGS. 5E and 12G-H). These findings demonstrate that dystrophic calcifications form contemporaneously with delayed monocyte/macrophage infiltration and delayed muscle regeneration in the setting of acute muscle injury and plasmin(ogen) deficiency.

Figure 5G:
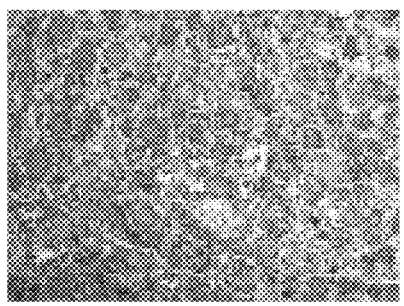
Figure 5G:
Figure 5H:
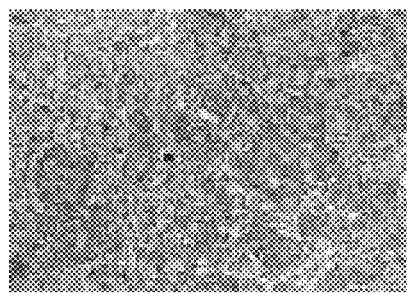
Figure 5H:
Figure 5I:
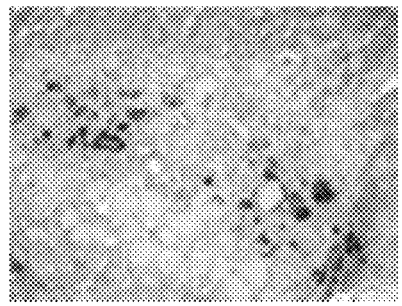
Figure 5I:
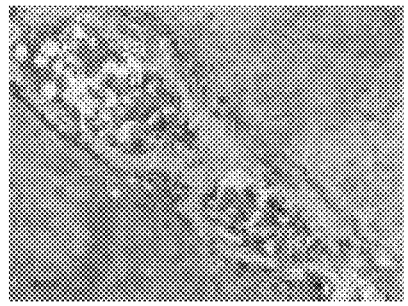
Figure 5J:
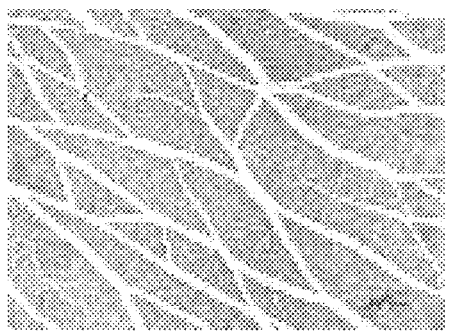
Figure 5J:
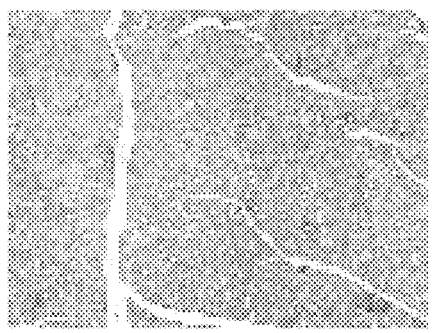
Figure 5K:
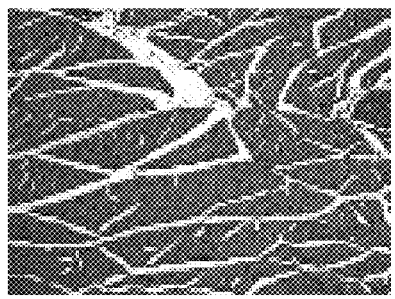
Figure 5K:
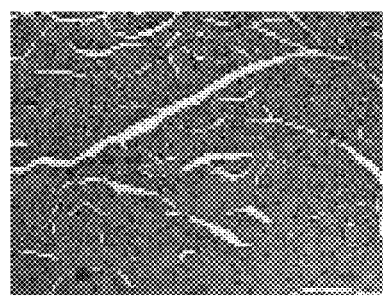
Figure 5L:
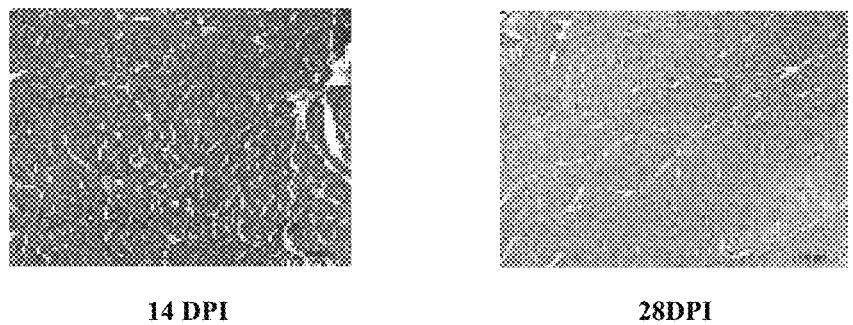
Figure 5M:
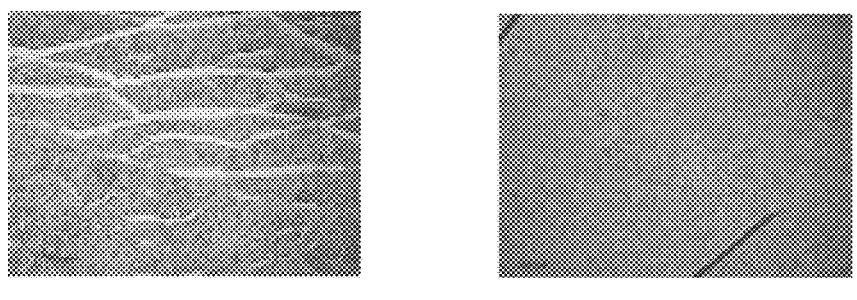
Figure 6A:
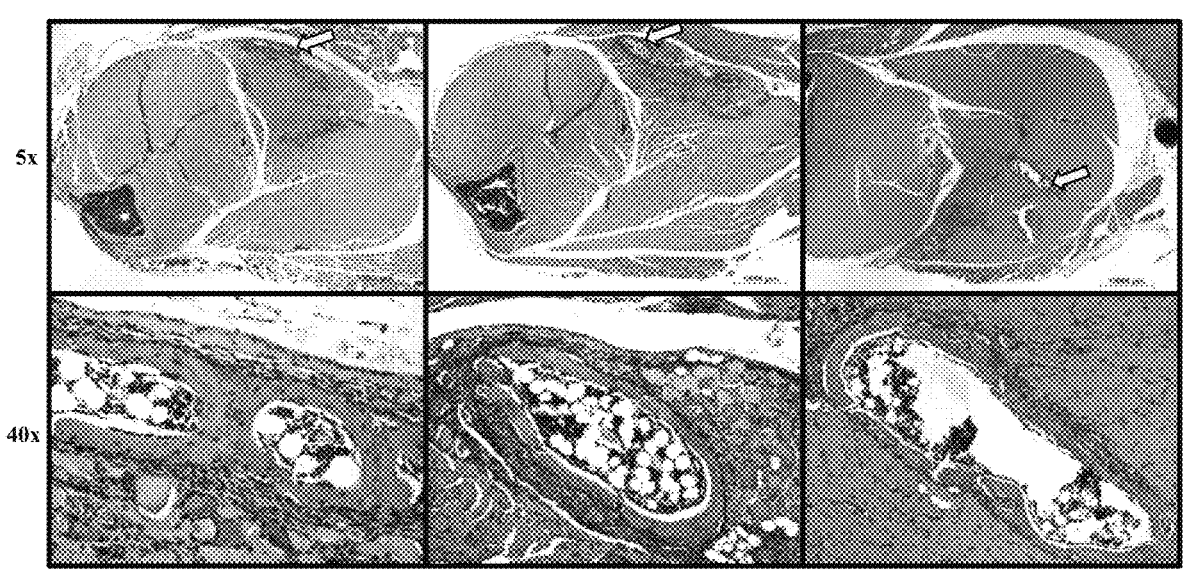
FIGS. 6A-B show images illustrating characterization of heterotopic ossification after muscle injury and plasminogen deficiency. (A) Representative H&E (5× magnification) showed woven bone forms exclusively within the posterior muscle compartment, separated by an intact fascial plane and distinct from the tibia and fibula 28 DPI in $Plg^{+/-}$ mice. Persistent dystrophic calcifications are scattered around the woven bone within the posterior muscle compartment. 40× magnification of the same section confirms woven bone with central hematopoiesis and rimming osteoblasts. (B) 2D cross sectional and axial μCT images demonstrated organized calcifications within the posterior muscle compartment distinct from, but morphologically consistent with the nearby tibia and fibula 28 DPI in $Plg^{+/-}$ mice. Adjacent to organized soft tissue calcifications are disorganized calcifications consistent with persistent dystrophic calcifications that surround HO histologically.
Figure 6B:
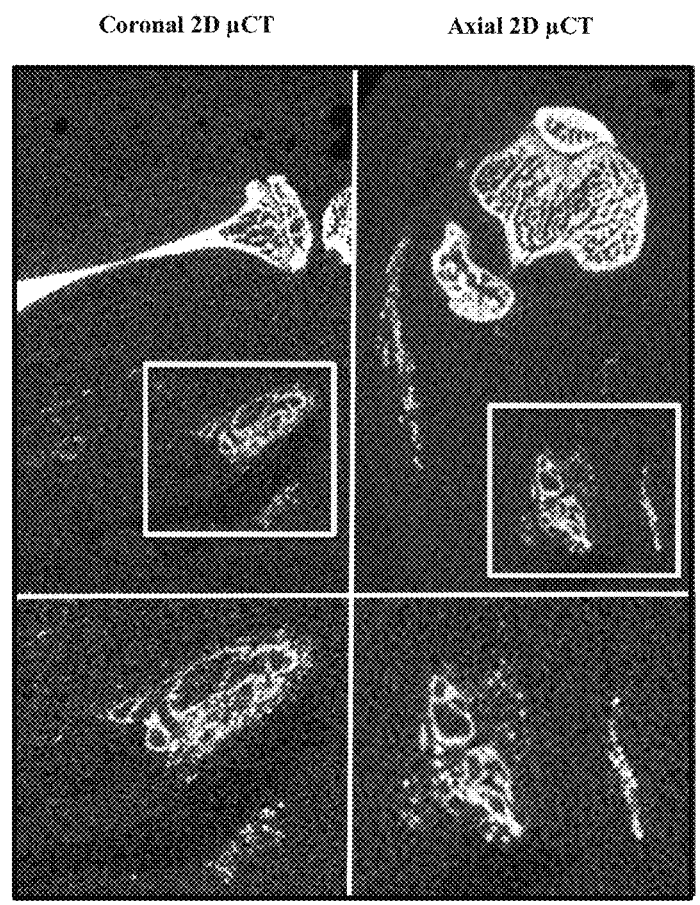

The evolution of dystrophic calcifications into HO was also evaluated histologically. Dystrophic calcifications, islands of hyaline chondroid matrix with chondrocytes, and TRAP-positive multinucleated giant cells were intermixed within injured muscle tissue of Plg$^{+/-}$ mice 14 DPI (FIGS. 5F-I and 13A). Two weeks later (28 DPI), mature woven bone with rimming osteoblasts and intertrabecular hematopoiesis was observed in Plg$^{+/-}$ injury sites (FIGS. 5G and 13B). The transition from a primitive chondroid matrix to mature woven bone is consistent with endochondral ossification, a histologic hallmark of HO. In contrast, injury sites in WT mice showed maturing striated muscle 28 DPI, consistent with effective tissue regeneration, without evidence of HO (FIGS. 5J-M). Histologic evaluation of HO at 28 DPI in Plg$^{+/-}$ mice demonstrated woven bone entirely contained with the posterior muscle compartment and distinct from the tibia and fibula (FIG. 6A). Two dimensional μCT showed the presence of circular condensed calcifications morphologically consistent with HO surrounded by disorganized calcifications consistent with dystrophic calcifications (FIG. 6B). Both abnormal findings were distinct from the cortex of nearby tibia and fibula. This data indicates that muscle injury in the setting of partial plasminogen deficiency is associated with persistent dystrophic calcification, and that persistent dystrophic calcifications are associated with subsequent development of HO within the injured muscle.

Plasmin Protease Activity Inhibits Deposition of Dystrophic Calcifications within Injured Muscle and Promotes Muscle Regeneration To test the hypothesis that soft tissue calcifications that form after traumatic injury are specifically attributable to a deficit in plasmin protease activity, and not some other biological activity associated with reduced plasminogen zymogen, we experimentally increased plasmin activity in vivo in the setting of global plasminogen reduction (Plg$^{+/-}$ mice) by targeting the primary inhibitor of plasmin protease activity—α2-antiplasmin (α2AP). Administration of α2AP ASO (α2AP$^{ASO}$) resulted in an 85% reduction of hepatic α2AP mRNA. Treatment of mdx/Plg$^{+/-}$ mice with α2AP$^{ASO}$ resulted in a marked reduction in soft tissue calcification compared to control ASO (control$^{ASO}$) treated mdx/Plg$^{+/-}$ mice (FIGS. 7A and 14), indicating that plasmin protease activity is a determinant of soft tissue calcification after myocyte injury.

Figure 7A:
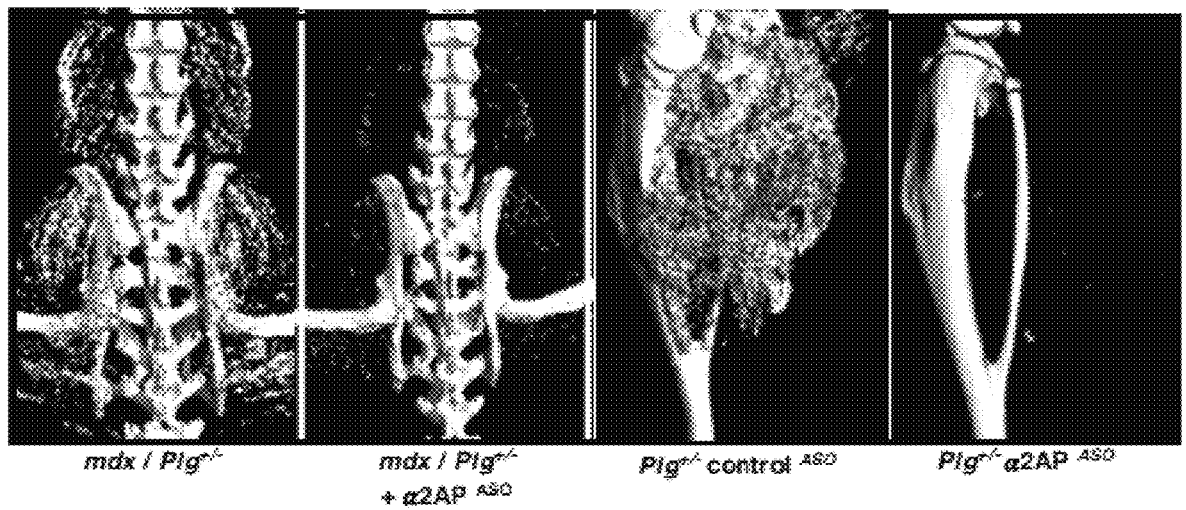
FIGS. 7A-D show graphs and images illustrating increasing plasmin activity preventing soft tissue calcification and rescuing muscle regeneration independent of fibrinolysis. (A) μCT reconstructions of mdx/$Plg^{+/-}$ mice treated with α2AP$^{ASO}$ showed markedly reduced soft tissue calcification compared to control mdx/$Plg^{+/-}$ mice. Similar reductions in soft tissue calcification were noted in CTX-injured $Plg^{+/-}$ mice treated with α2AP$^{ASO}$ relative to control$^{ASO}$. (B) Representative histologic images of CTX-injured $Plg^{+/-}$ mice treated with control$^{ASO}$ or α2AP$^{ASO}$. α2AP$^{ASO}$ treatment, but not control$^{ASO}$, promoted fibrin(ogen) clearance (fibrin-red/DAPI-blue, 7 DPI), prevented dystrophic calcification (Von Kossa-black, 7 DPI), restored macrophage/monocyte cell infiltrate (F4/80, 3 DPI) and restored muscle regeneration (H&E, 7 DPI). These data indicate that plasmin protease activity is essential for limiting dystrophic calcification and promoting muscle regeneration. (C) μCT reconstructions of CTX-injured $Plg^{+/-}$ mice treated with control$^{ASO}$ ($Plg^{+/-}$ control$^{ASO}$) or fibrinogen$^{ASO}$ ($Plg^{+/-}Fbg^{Low}$) revealed marked soft tissue calcification formation 7 DPI. Mice genetically deficient in fibrinogen also developed HO when treated with a plasminogen$^{ASO}$($Fbg^{-/-}Plg^{Low}$). (D)
Figure 7B:
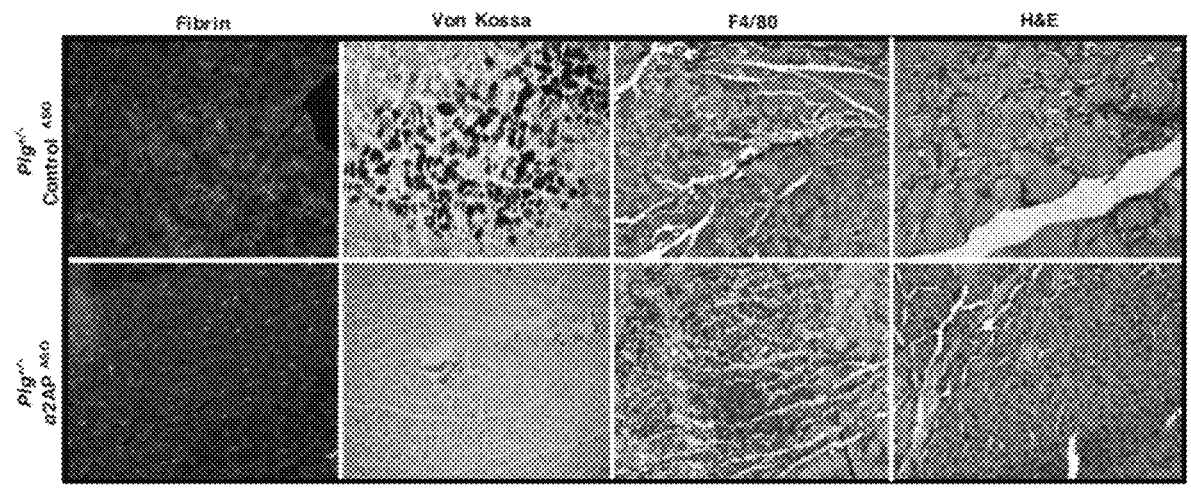
Figure 15A:
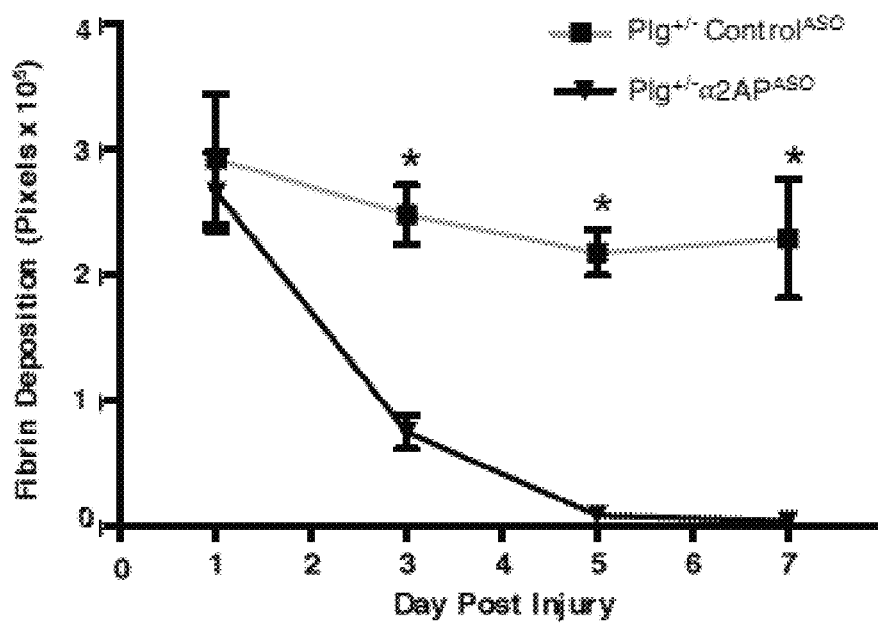
Figure 15B:
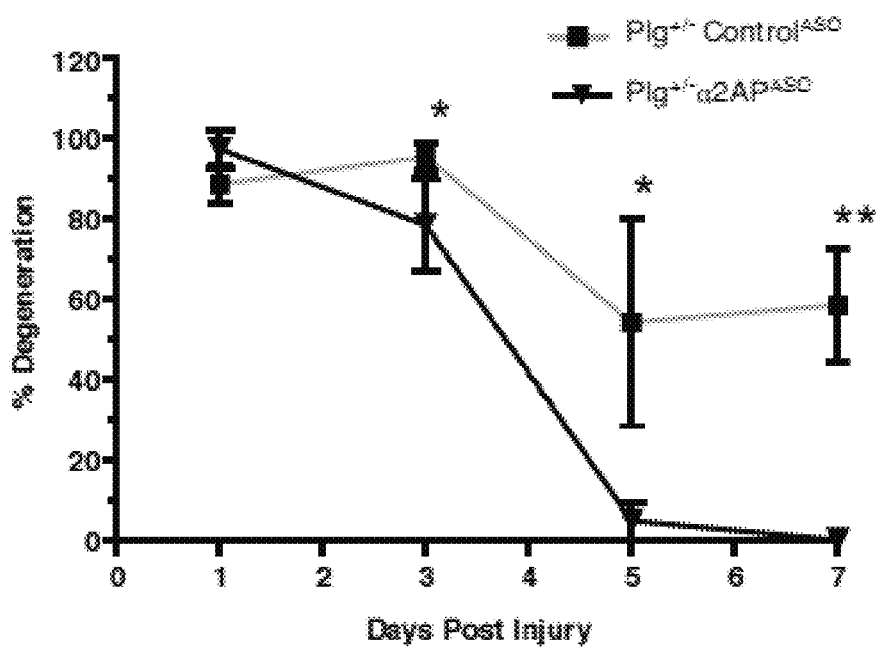
Figure 15C:
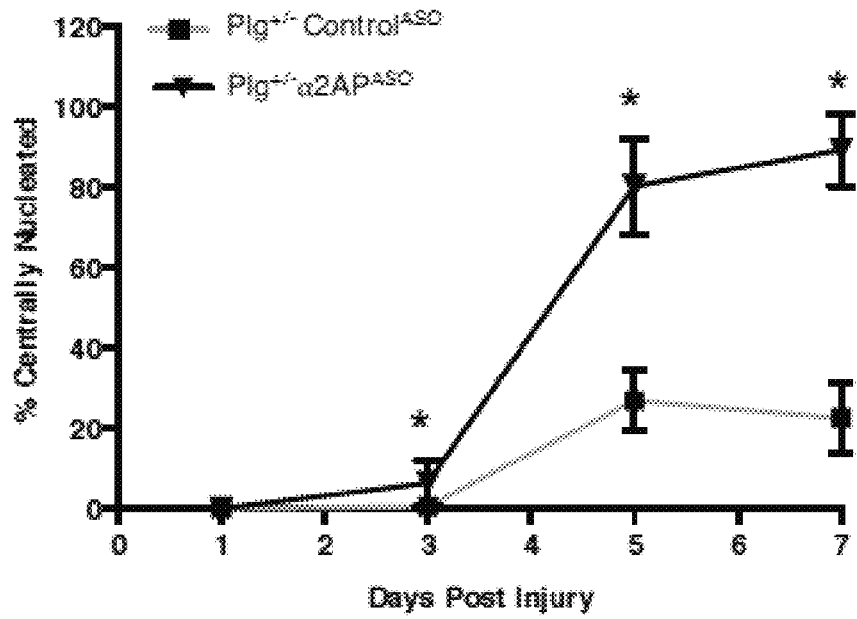
Figure 15D:
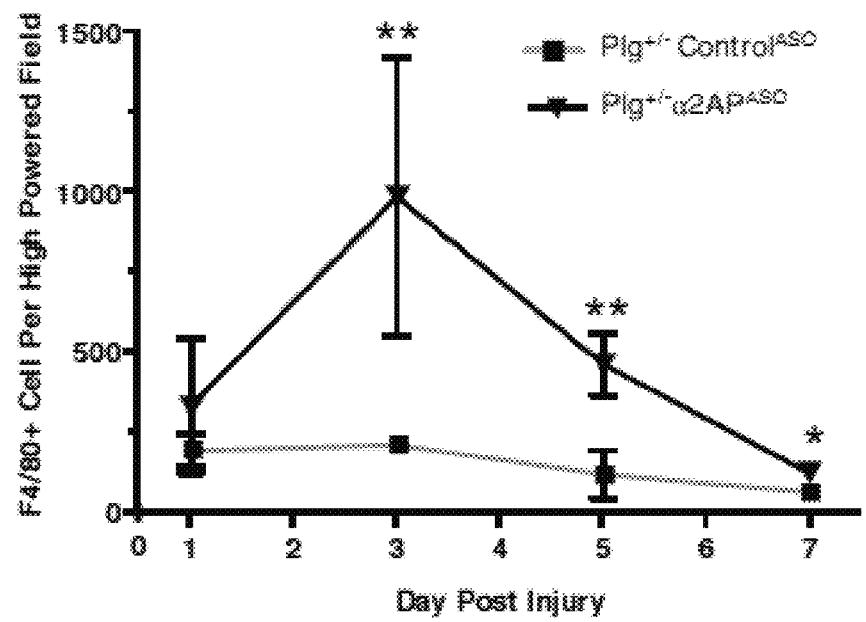
Figure 15E:
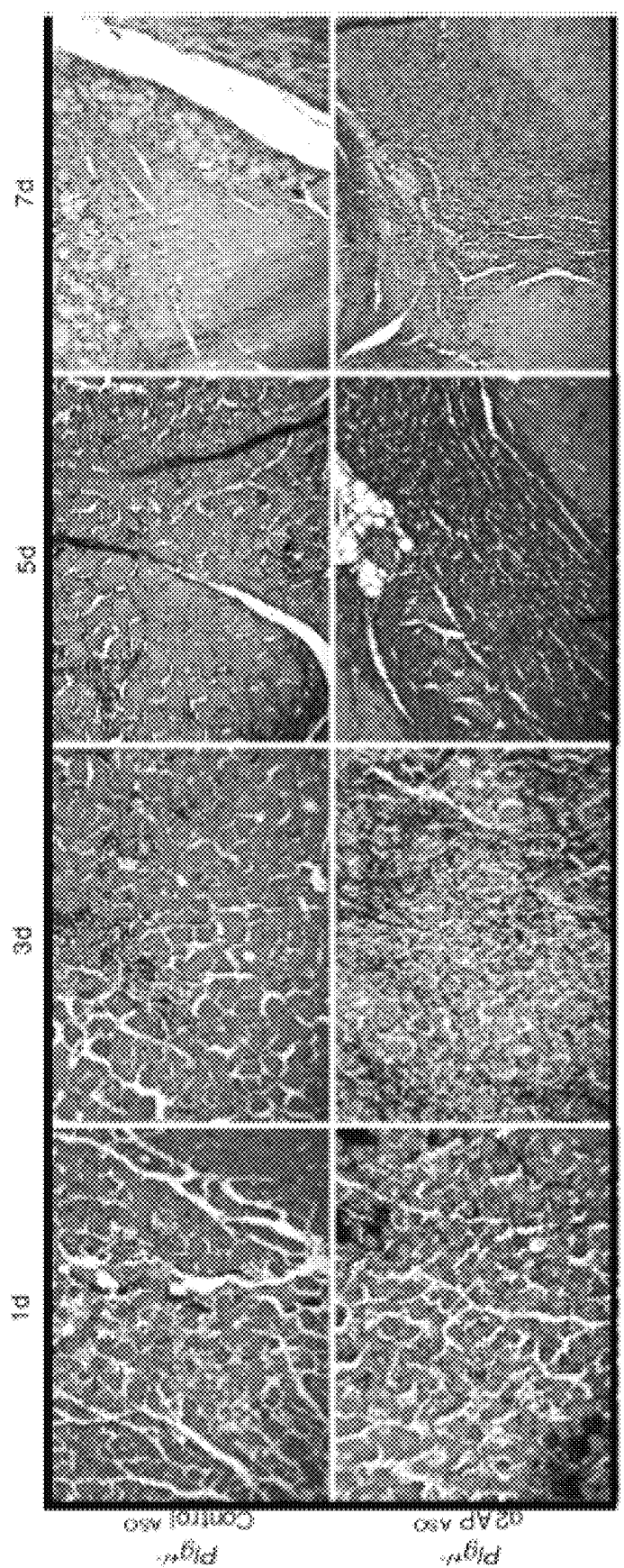

To provide further insight regarding the molecular mechanisms by which plasmin protease activity prevents soft tissue calcification, we studied the effects of increasing plasmin activity on the injury microenvironment in Plg$^{+/-}$ mice after acute CTX-induced muscle injury. Treatment of Plg$^{+/-}$ mice with α2AP$^{ASO}$ again resulted in a marked reduction in soft tissue mineralization compared to control ASO (control$^{ASO}$) treatment (FIG. 7A). Comparative studies of local fibrin deposition following acute muscle injury confirmed that plasmin activity was a primary determinant of fibrin clearance (fibrinolysis) (FIGS. 7B and 15A). Histologic analysis showed that α2AP$^{ASO}$ treatment limited the degree of dystrophic calcification within necrotic skeletal muscle (FIG. 7B). In addition, enhanced plasmin activity promoted monocyte/macrophage infiltration into the site of injury and significantly increased myofiber regeneration (FIGS. 6B and 15A-E). Together these data indicate that plasmin protease activity promotes local fibrinolysis, monocyte/macrophage infiltration, and muscle regeneration, in addition to inhibiting deposition of dystrophic calcifications.

Figure 7C:
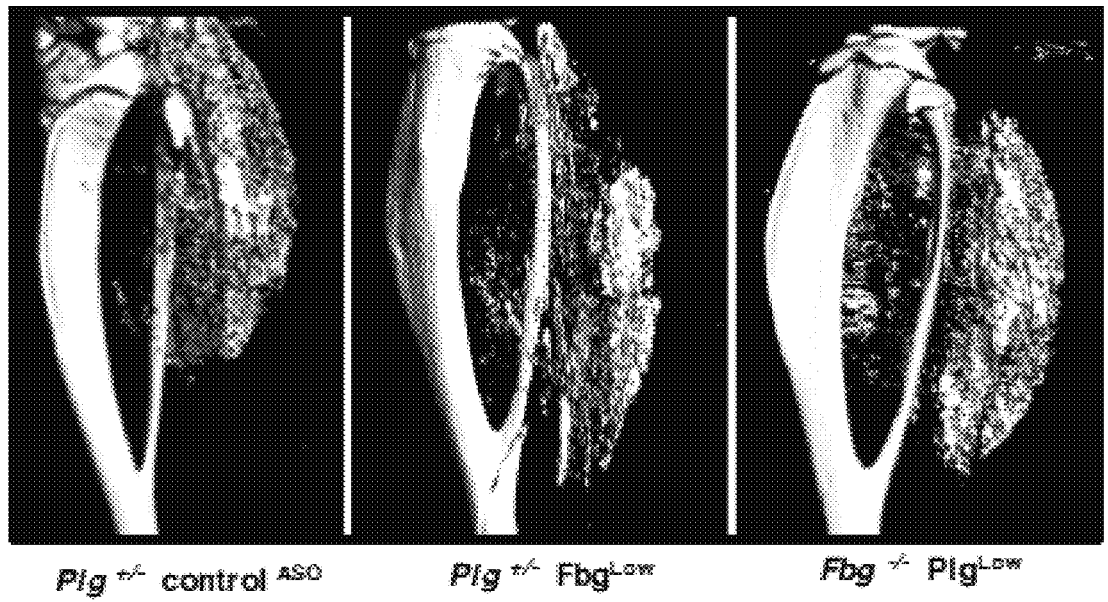
Figure 7D:
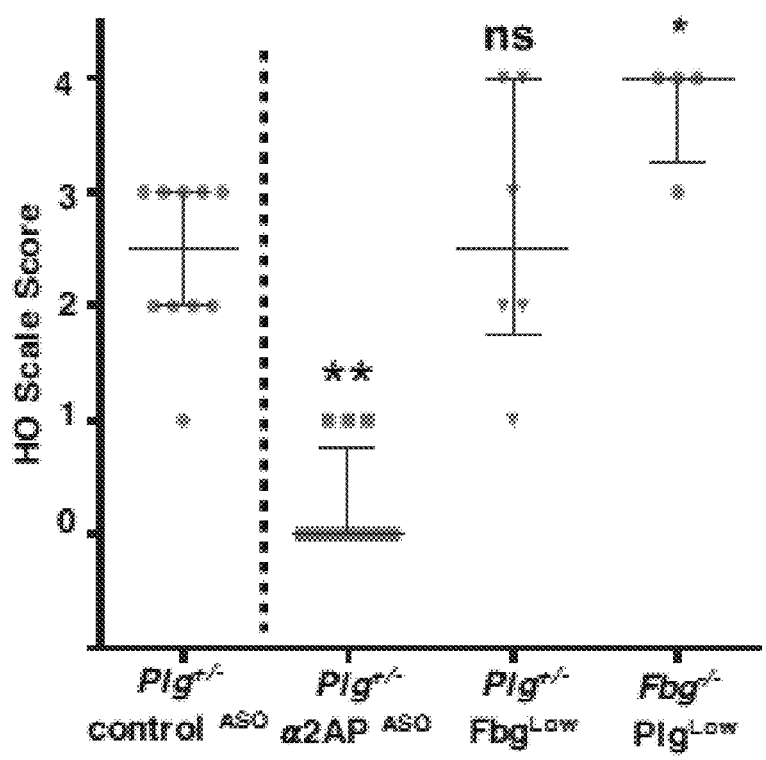

Plasmin Regulates Dystrophic Calcification Independent of its Canonical Fibrinolytic Function Reduction in plasmin activity may promote dystrophic calcification and subsequent HO through multiple molecular mechanisms. For example, insufficient fibrin clearance (hypofibrinolysis) might result in a persistent fibrin scaffold that could act as a nucleating agent for calcium phosphate precipitation. However, we found that knock-down of fibrinogen expression using a fibrinogen-directed ASO (Fb-g$^{ASO}$) failed to prevent soft tissue calcification in Plg$^{+/-}$ mice following muscle injury (FIGS. 7C-D). To further exclude a possible role of fibrin and fibrinolysis in soft tissue calcification, complete genetic fibrinogen knockout mice (Fbg$^{-/-}$ mice) were treated with Plg$^{ASO}$. In these fibrinogen/plasminogen-deficient mice, robust soft tissue calcification was observed similar to that seen in animals deficient in plasminogen alone (FIGS. 7C-D). Thus, the prevention of soft tissue calcification after injury appears to depend upon a plasmin function outside of fibrin cleavage.

Plasmin Prevents HO by Limiting Deposition of Osteoinductive Dystrophic Calcification While Promoting Muscle Regeneration Histologic analysis of the muscle injury site during the acute phase of injury (1-7 DPI) demonstrated that early soft tissue calcification is principally attributable to formation of dystrophic calcifications within necrotic myocytes (FIGS. 5A-M). By 14 DPI, chondroid matrix is observed interspersed with persistent dystrophic calcifications. By 28 DPI, these deposits are replaced by woven bone. As dystrophic calcifications precede endochondral ossification, are spatially interspersed with foci of chondroid matrix, and disappear with formation of woven bone at the injury site, persistent dystrophic calcifications represent a potential osteoinductive mechanism for HO.

Given its universal presence in mice with deficient plasmin activity, it was therefore hypothesized that exuberant and persistent dystrophic calcification is a unique product of combined muscle injury and deficient plasmin activity and acts as a stimulus for subsequent endochondral ossification (FIG. 8A). Since dystrophic calcification of soft tissue is inhibited by endogenous pyrophosphate as well as pyrophosphate analogues, we treated Plg$^{+/-}$ mice sustaining a CTX-induced injury with a non-hydrolysable synthetic pyrophosphate analogue. Pyrophosphate analogue treatment significantly reduced soft tissue calcification in this model and prevented HO at 28 DPI, similar to the effects observed with α2AP$^{ASO}$ treatment (FIGS. 8B-C). Thus, these data indicate that plasmin prevents HO by limiting dystrophic calcification in muscle following injury.

Deficient plasmin activity caused a number of aberrations during the acute phase of muscle injury: persistent dystrophic calcification and necrotic debris, deficient macrophage infiltration, and deficient myocyte regeneration (FIGS. 5B-E). HO was a delayed complication of this disturbed healing microenvironment and could be a result of all or a subset of these pathologenetic factors. To determine if plasmin's role in limiting dystrophic calcification determines subsequent myogenesis we evaluated late muscle regeneration in mice deficient in plasminogen also treated with a pyrophosphate analogue. Histologic analysis 28 DPI of Plg$^{+/-}$ mice demonstrated that although pyrophosphate analogue treatment prevented dystrophic calcification, and subsequent HO, muscle necrosis was not resolved and myogenesis did not ensue (FIG. 8C). On the other hand, restoring plasmin activity (α2AP$^{ASO}$-treated mice) limited dystrophic calcification (and subsequent HO) (FIGS. 7A-D), resolved muscle necrosis, and promoted muscle regeneration (FIG. 8C). These data provide compelling evidence that plasmin is essential to promote myogenesis and prevent dystrophic calcification through alternative pathways.

Figure 9A:
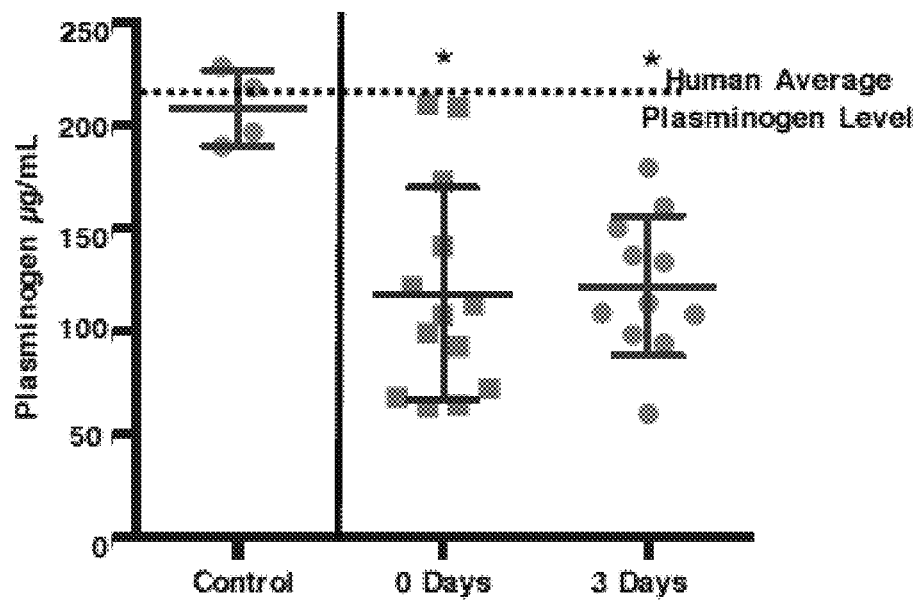
Figure 9B:
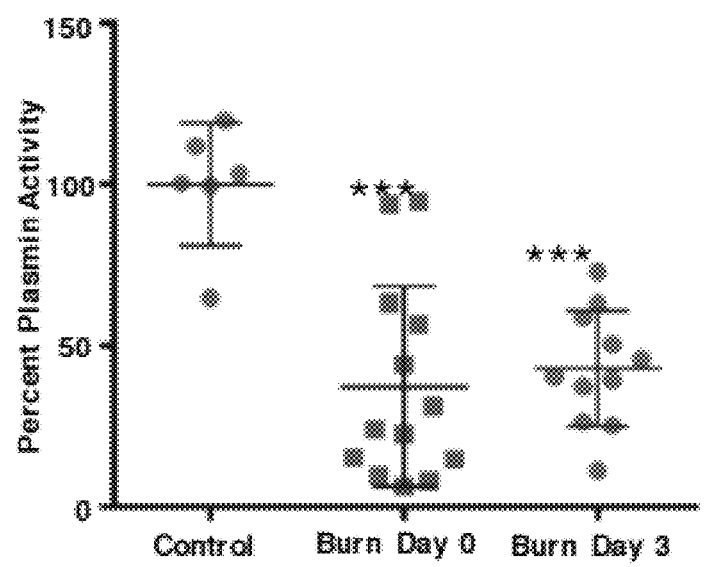
Figure 9C:
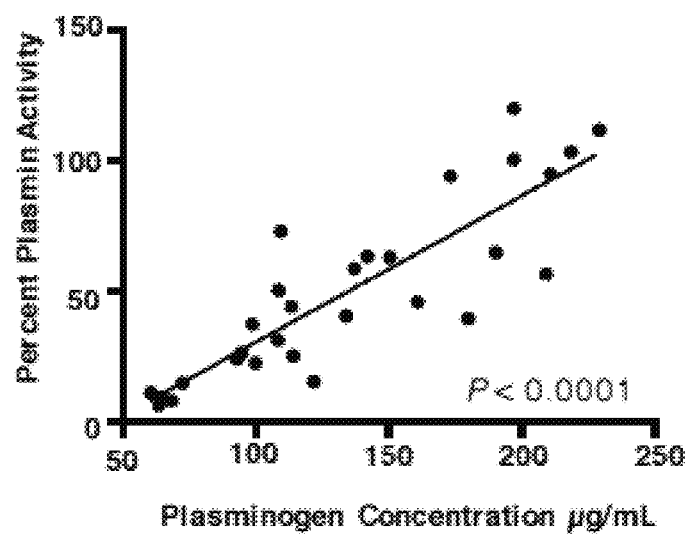
Figure 9D:
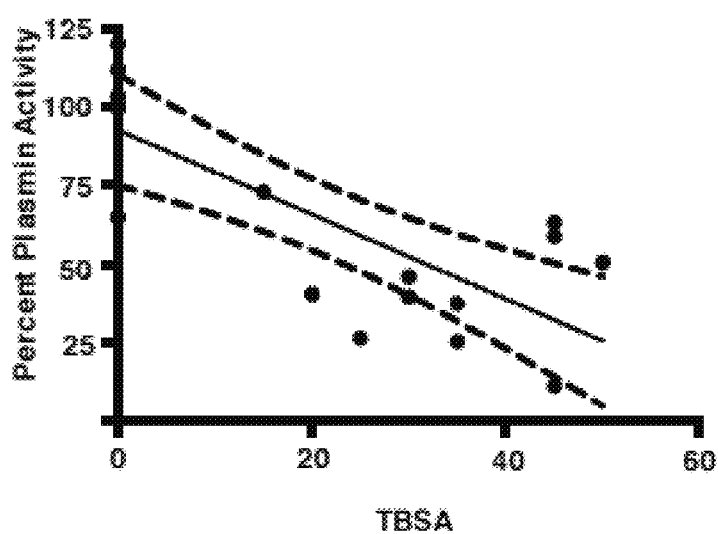
Figure 9E:
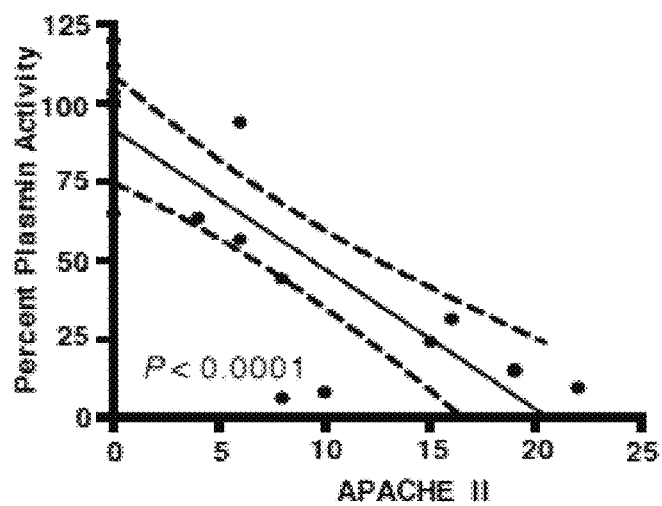
Figure 10A:
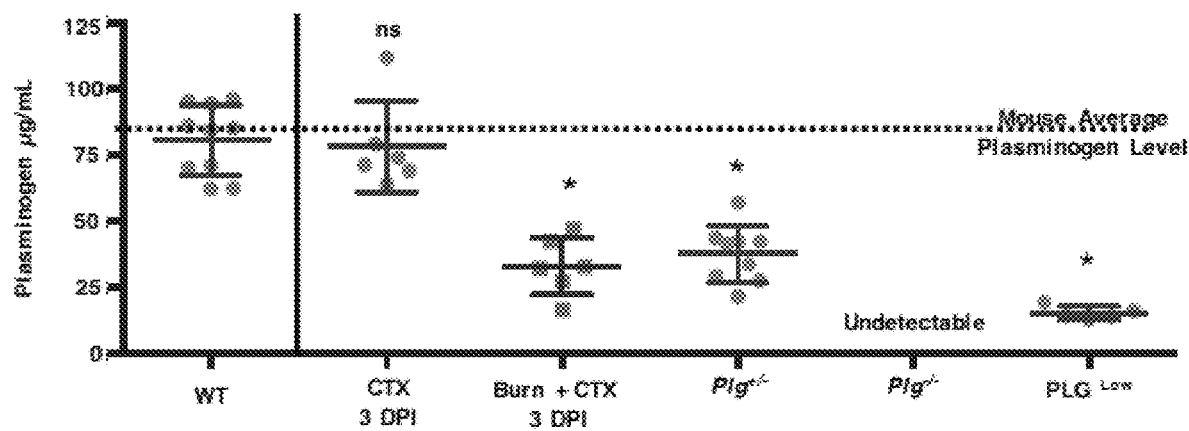
Figure 10B:
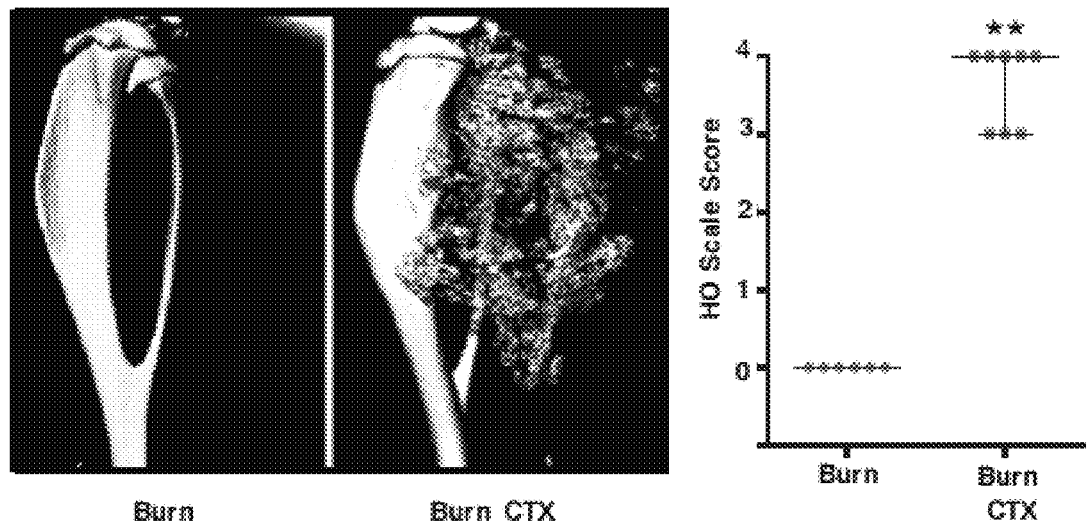
Figure 10C:
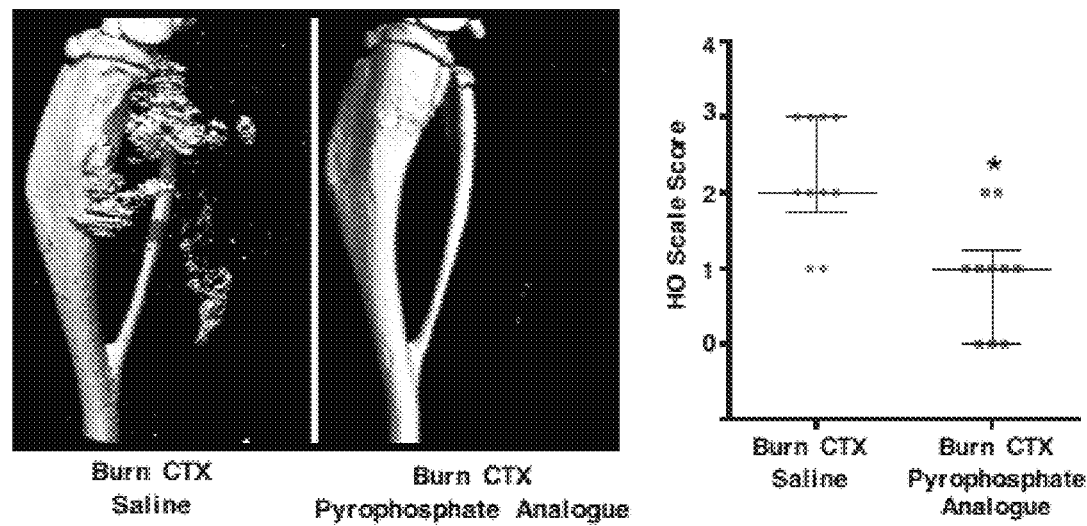

Combined Cutaneous Burn and Muscle Injury Depletes Plasminogen Levels and Results in HO Given that muscle injury in the setting of severe burn or blast injury is associated with HO and that these patients are also hypofibrinolytic, we hypothesized that HO is a sequela of two prerequisites: muscle trauma and reduced systemic plasmin activity. To further explore this hypothesis, we measured plasminogen levels and plasmin activity in plasma obtained from burn patients. Significant hypoplasminogenemia correlated with reduced plasmin activity following burn injury and persisted through 3 days post burn (FIGS. 9A-C). Additionally, the extent of hypoplasminogenemia in these patients correlated with both Total Burn Surface Area (TBSA) and the severity of injury as measured by APACHE II (FIGS. 9D-E). At 3 DPI, injured WT mice simulating the clinical scenario of superimposed burn and muscle injury often associated with HO in human patients were also profoundly hypoplasminogenemic, with circulating plasminogen levels approximating that of Plg$^{+/-}$ mice (FIG. 10A). Combined burn and CTX-injected WT mice showed significant radiographic evidence of HO compared to burn alone (FIG. 10B). As determined in the Plg$^{+/-}$ mice sustaining a CTX-induced injury, supplementation of combined burn/muscle injury with a pyrophosphate analogue also prevented HO (FIG. 10C) implicating the formation of dystrophic calcification as the determining factor of HO in this combined cutaneous burn and muscle injury scenario. These findings demonstrate that reduced plasmin activity and muscle injury associated with combined burn and CTX-induced muscle injury is sufficient to cause HO, thereby providing a clinically relevant and instructive model for trauma-induced HO.

Figure 10D:
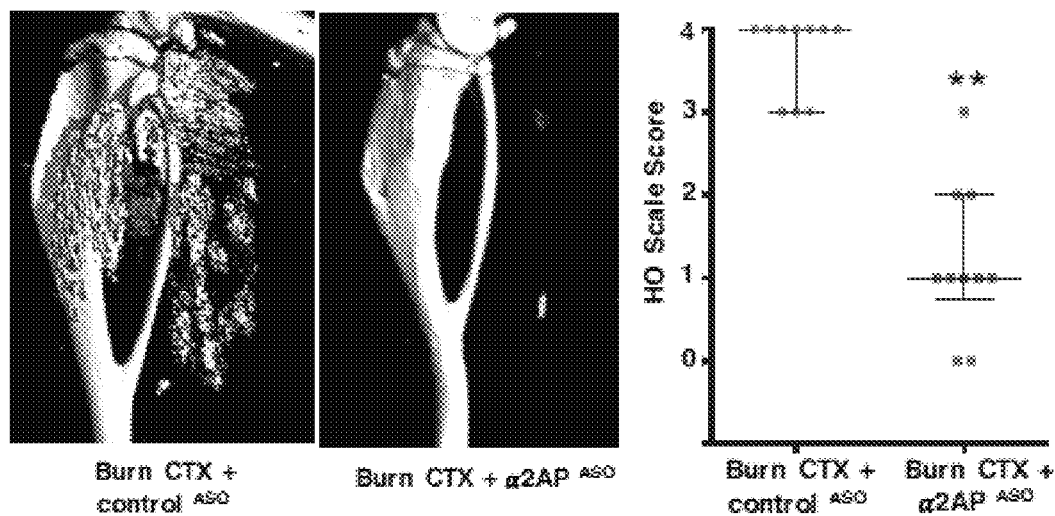

Since enhancing plasmin activity in our other experimental models prevented HO, we explored the effects of α2AP$^{ASO}$ on this clinical model of HO. The incidence and severity of HO in α2AP$^{ASO}$-treated mice was significantly decreased compared to control$^{ASO}$-treated combined burn/muscle injury mice (FIG. 10D). This demonstrated that increased plasmin activity (mediated through inhibition of α2AP) can prevent HO following combined burn/muscle injury. In summary, these data provide compelling evidence that combined burn and muscle injury leads to derangements in both the capacity for plasmin-mediated proteolysis and HO, and that this HO can be prevented by pharmacologically inhibiting a single factor—α2AP.

Discussion

The present studies disclose an unexpected and new role for plasmin-mediated proteolysis in soft tissue calcification distinct from its classic role in fibrinolysis. Specifically, a critical threshold of plasmin activity is essential for prevention of dystrophic calcification following muscle injury. Dystrophic calcifications formed in the setting of deficient plasmin activity are sufficient to promote endochondral ossification and HO. In the setting of decreased circulating plasminogen, pharmacologic intervention enhancing the proteolytic activity of plasmin by targeting the key plasmin-specific inhibitor, α2AP, prevents HO by limiting dystrophic calcification. At the same time, enhancing plasmin activity promotes clearance of necrotic myocytes and restores muscle regeneration in vivo. These results establish the central role of plasmin, and thereby the plasminogen activation system, in promoting muscle regeneration and protecting against soft tissue calcification in injured skeletal muscle.

One of the major findings of this work is that plasmin activity protects injured muscle from persistent dystrophic calcification independent of its canonical role in fibrinolysis. Extravascular fibrin deposition is a universal feature of muscle injury and fibrin accumulation is a key pathogenic mechanism in a number of phenotypes associated with plasmin deficiency. However, fibrinogen depletion failed to prevent soft tissue calcification associated with plasmin deficiency, indicating that one or more plasmin substrates other than fibrin protect against soft tissue calcification. Plasmin is a promiscuous serine protease, and multiple other plasmin targets may be responsible for its protective effects, such as growth factors, extracellular matrix proteins, or other protease zymogens[47-52]. It is possible that plasmin exhibits its influence indirectly via alterations of hormones known to regulate calcium and/or phosphate metabolism such as PTH, FGF23 or Vitamin D. Additionally, plasmin may process targets known to have direct anti-mineralization function. In support of this, plasmin was recently demonstrated as a principal activator of the anti-mineralization protein osteopontin. This investigation did not quantify additional hormones, growth factors or metabolites previously associated with soft tissue calcification and will require additional investigation. Defining the plasmin substrates(s) that inhibit soft tissue calcification will be instrumental in fully resolving the pathogenic mechanism(s)

involved. However, exclusion of a fibrin-dependent mechanism provides a key foundation for further studies in this regard.

Identifying plasmin as a key determinant of HO by protecting against persistent dystrophic calcification redefines the understanding of trauma-associated HO. Moreover, it identifies novel therapeutic targets to prevent HO. Dystrophic calcifications were observed in plasmin-competent mice following injury. However, calcifications were much less conspicuous than in plasmin-deficient mice and were eventually resorbed during tissue repair. Resorption of dystrophic calcifications and rapid clearance of necrotic myocytes in plasmin-competent mice correlated with infiltration of the injury site by monocytes/macrophages. Notably, monocytes and macrophages are capable of resorbing nontrabecular calcified tissue both directly by phagocytosis and indirectly by secreting carbonic anhydrase II and osteopontin. Previous studies have also documented that plasmin can promote monocyte/macrophage migration as well as phagocytosis. When macrophages are unable to engulf their target, they exhibit so-called "frustrated phagocytosis" that has been hypothesized to drive macrophage fusion and osteoclast-like differentiation. TRAP-positive staining has been associated with multi-nucleated giant cells in addition to osteoclasts, and we observed TRAP-positive cells intermixed with persistent dystrophic calcifications preceding woven bone formation in plasmin-deficient mice. Our data suggests that decreased plasmin activity alters critical, macrophage-dependent resorption of dystrophic calcifications and the appearance of TRAP-positive cells could indicate a compensatory fusion for altered macrophage function. Additionally, dystrophic calcifications formed more rapidly and were more exuberant after injury in plasmin-deficient mice, indicating that in addition to promoting resorption, plasmin activity also prevents the initial deposition of dystrophic calcifications. We therefore speculate that plasmin protects against HO by preventing formation of dystrophic calcifications within the injured muscle microenvironment, as well as promoting macrophage/monocyte-dependent mechanisms for resorbing dystrophic calcifications.

Without plasmin, dystrophic calcifications persisted at the injury site and stimulated endochondral ossification. Importantly, these results were obtained without experimental manipulation of the BMP signaling pathway. As BMP expression is required for all endochondral ossification processes (biologic or pathologic), BMP signaling is likely upregulated in this HO model as well. However, we postulate its effect would be to promote ossification downstream of the initiating effects of decreased plasmin activity and dystrophic calcification, and not the primary pathogenetic mechanism in formation of soft tissue calcification. Previous studies, and the results within, argue that the osteoinductive nature of dystrophic calcifications, similar to that of calcified cartilage, innately promote invading mesenchymal stem cells intended for myocyte regeneration to undergo osteogenic differentiation instead. Supporting this theory, muscle-derived mesenchymal stem cells within the injury microenvironment were shown to primarily contribute to HO formation. This theory is further supported by the finding that administering a non-hydrolysable pyrophosphate analogue, a potent inhibitor of dystrophic calcification, completely prevented HO in plasminogen-deficient muscle injury models. These findings suggest that pharmacologic strategies targeting plasmin activity, instead of systemically inhibiting bone regenerative pathways, may effectively prevent HO.

Linking plasmin to fibrinolysis-independent prevention and resorption of dystrophic calcifications fundamentally changes the current paradigm of soft tissue calcification beyond skeletal muscle HO. The present findings are strikingly reminiscent of studies demonstrating a fibrin(ogen)-independent mechanism of persistent centrilobular liver necrosis and dystrophic calcification in plasminogen-deficient mice following hepatoxin-induced liver injury[31]. Furthermore, these findings suggest that similar molecular mechanisms involving chronic tissue injury, plasmin activity, and soft tissue calcification occur in other diseases such as atherosclerosis and renal calcinosis. For example, increased expression of plasminogen activator inhibitor-1 (PAI-1) in human atherosclerotic vessels parallels the severity of atherosclerosis, and PAI-1 deficiency protects against atherosclerosis in apolipoprotein E (ApoE) genetic knockout mice[68,69]. The ability of PAI-1 to modify levels of soft tissue calcification was initially interpreted as potentially independent of its inhibition of plasmin activation. However, given our data linking plasmin activity with dystrophic calcification of soft tissue, we propose that PAI-1 overexpression decreases plasmin-mediated protection against calcium deposition. Supporting this interpretation, Xiao et al. demonstrated that plasminogen deficiency exacerbates atherosclerosis in ApoE knockout mice. An additional example linking plasmin activity and calcific disease can be found in the kidney where deficiency in Klotho, a protein required for fibroblast growth factor 23 (FGF23)-mediated phosphate excretion in the distal tubules, results in over-expression of PAI-1 and extensive renal calcification. Remarkably, renal calcification induced by Klotho deficiency can be ameliorated by reducing PAI-1 levels. We speculate that dystrophic calcification is a predictable pathophysiologic outcome of acute or chronic injury where events (e.g., inordinate systemic plasminogen consumption) result in insufficient local plasmin activity.

While plasminogen deficiency caused persistent dystrophic calcification in both acute and chronic muscle injury models, only the acute injury model subsequently developed HO. This dichotomy presents an opportunity for future evaluation of the specific factors in different injury microenvironments that either prevent or promote the transition from dystrophic calcification to HO. We hypothesize that the disparity in HO development in these different models stems from a severity of tissue injury and more intense or prolonged tissue hypoxia in the acute CTX injury model compared to the chronic mdx injury model, since hypoxia increases the incidence of HO through promotion of cartilaginous intermediates for endochondral ossification.

Our findings also amend the long-standing and prevailing view that HO principally develops primarily from aberrant "gain of function" activation of bone-related growth factor signaling pathways. Instead, we propose a "loss of function" mechanism: HO can result from a deficiency of plasmin's protective effects that normally serve to limit deposition of dystrophic calcifications within injured muscle tissue. There is also substantial clinical evidence that hypofibrinolysis occurs in traumatic injuries associated with HO, including burn and spinal cord injuries. Future studies are necessary to establish the clinical physiology of acquired plasmin deficiency in both acute traumatic injuries associated with HO as well as chronic inflammation associated with soft tissue calcification (atherosclerosis, tumoral calcinosis, renal calcinosis, etc.). Still, these findings have significant implications for patients at risk for trauma-induced HO. Current and proposed treatments for HO, including anti-inflammatory agents, pyrophosphate analogues, ionizing radiation therapy, BMP antagonists, and retinoic acid receptor agonists all have the undesirable adverse effect of disrupting systemic bone homeostasis and inhibiting fracture repair. In stark contrast to these current or proposed therapies, we have previously reported that plasmin activity is essential for fracture repair and bone homeostasis. Future studies are required to identify and investigate the complications and clinical feasibility of reducing α2AP to increase plasmin activity. However, our proof-of-principle studies preventing HO by augmenting plasmin activity through targeting α2AP in vivo represent the first pharmacological strategy with potential to suppress HO and promote muscle regeneration without sacrificing bone health and regeneration.

Here, we show that plasmin protease activity prevents dystrophic calcification within injured skeletal muscle independent of its canonical fibrinolytic function. After muscle injury, dystrophic calcifications either can be resorbed during the process of tissue healing, persist, or become organized into mature bone (HO). Without sufficient plasmin activity, dystrophic calcifications persist after muscle injury and are sufficient to induce HO. Downregulating the primary inhibitor of plasmin (α2-antiplasmin) or treating with pyrophosphate analogues prevents dystrophic calcification and subsequent HO in vivo. Since plasmin also supports bone homeostasis and fracture repair, increasing plasmin activity represents the first pharmacologic strategy to prevent soft tissue calcification without adversely affecting systemic bone physiology or concurrent muscle and bone regeneration.

Additionally, linking plasmin to the fibrinolysis-independent prevention and resolution of dystrophic calcification fundamentally changes the current paradigm of soft tissue calcification beyond skeletal muscle HO. Now that we have demonstrated that dystrophic calcification is a predictable pathophysiologic outcome of acute or chronic injury where events (e.g., inordinate systemic plasminogen consumption) have resulted in insufficient local plasmin activity. Further, inadequate local plasmin activity constitutes a previously unappreciated cause of calcific disease in a multitude of tissues (atherosclerosis, renal calcification etc).

Throughout this document, various references are mentioned. All such references are incorporated herein by reference, including the references set forth in the following list:

REFERENCES

1. D. C. Covey, Combat orthopaedics: a view from the trenches. *The Journal of the American Academy of Orthopaedic Surgeons* 14, S10 (2006).
2. D. Gajewski, R. Granville, The United States Armed Forces Amputee Patient Care Program. *The Journal of the American Academy of Orthopaedic Surgeons* 14, S183 (2006).
3. E. R. Nelson, V. W. Wong, P. H. Krebsbach, S. C. Wang, B. Levi, Heterotopic ossification following burn injury: the role of stem cells. Journal of burn care & research: official publication of the American Burn Association 33, 463.
4. J. A. Forsberg et al., Heterotopic ossification in high-energy wartime extremity injuries: prevalence and risk factors. The Journal of bone and joint surgery. American volume 91, 1084 (2009)
5. M. R. Urist, Bone: formation by autoinduction. Science 150, 893 (Nov. 12, 1965)
6. M. R. Urist, A. Mikulski, A. Lietze, Solubilized and insolubilized bone morphogenetic protein. Proceedings of the National Academy of Sciences of the United States of America 76, 1828 (April, 1979)
7. J. M. Wozney et al., Novel regulators of bone formation: molecular clones and activities. Science 242, 1528 (Dec. 16, 1988).
8. F. S. Kaplan et al., Fibrodysplasia ossificans progressiva. Best practice & research. Clinical rheumatology 22, 191 (March, 2008).
9. E. J. Mitchell, J. Canter, P. Norris, J. Jenkins, J. Morris, The genetics of heterotopic ossification: insight into the bone remodeling pathway. J Orthop Trauma 24, 530 (September, 2010).
10. J. Chalmers, D. H. Gray, J. Rush, Observations on the induction of bone in soft tissues. The Journal of bone and joint surgery. British volume 57, 36 (1975).
11. S. Agarwal et al., Inhibition of Hiflalpha prevents both trauma-induced and genetic heterotopic ossification. Proceedings of the National Academy of Sciences of the United States of America 113, E338 (Jan. 19, 2016).
12. H. Fleish, W. F. Neuman, Mechanisms of calcification: role of collagen, polyphosphates, and phosphatase. Am J Physiol 200, 1296 (June, 1961).
13. T. Gillman, R. A. Grant, M. Hathorn, Histochemical and chemical studies of calciferol-induced vascular injuries. Br J Exp Pathol 41, 1 (February, 1960).
14. H. Fleisch, J. Maerki, R. G. Russell, Effect of pyrophosphate on dissolution of hydroxyapatite and its possible importance in calcium homeostasis. Proc Soc Exp Biol Med 122, 317 (June, 1966).
15. R. M. Goodman et al., Pseudoxanthoma Elasticum: A Clinical and Histopathological Study. Medicine (Baltimore) 42, 297 (September, 1963).
16. H. Yuan et al., Osteoinduction by calcium phosphate biomaterials. J Mater Sci Mater Med 9, 723 (December, 1998)
17. U. Ripamonti, Osteoinduction in porous hydroxyapatite implanted in heterotopic sites of different animal models. Biomaterials 17, 31 (January, 1996).
18. D. Le Nihouannen et al., Ectopic bone formation by microporous calcium phosphate ceramic particles in sheep muscles. Bone 36, 1086 (June, 2005).
19. M. J. Cohen et al., Critical role of activated protein C in early coagulopathy and later organ failure, infection and death in trauma patients. Annals of surgery 255, 379 (February, 2012).
20. B. L. Enderson, J. P. Chen, R. Robinson, K. I. Maull, Fibrinolysis in multisystem trauma patients. The Journal of trauma 31, 1240 (September, 1991).
21. J. V. Sorensen, Levels of fibrinolytic activators and inhibitors in plasma after severe trauma. Blood coagulation & fibrinolysis: an international journal in haemostasis and thrombosis 5, 43 (February, 1994).
22. K. Zouaoui Boudjeltia et al., Relationship between CRP and hypofibrinolysis: Is this a possible mechanism to explain the association between CRP and outcome in critically ill patients? Thrombosis journal 2, 7 (Sep. 30, 2004).
23. E. I. Deryugina, J. P. Quigley, Cell surface remodeling by plasmin: a new function for an old enzyme. Journal of biomedicine & biotechnology 2012, 564259 (2012).
24. X. Gu et al., Plasminogen K5 activates mitochondrial apoptosis pathway in endothelial cells by regulating Bak and Bcl-x(L) subcellular distribution. Apoptosis: an international journal on programmed cell death 16, 846 (August, 2011).

25. E. Creemers et al., Disruption of the plasminogen gene in mice abolishes wound healing after myocardial infarction. The American journal of pathology 156, 1865 (June, 2000).

26. Y. Gong, Y. Zhao, Y. Li, Y. Fan, J. Hoover-Plow, Plasminogen regulates cardiac repair after myocardial infarction through its noncanonical function in stem cell homing to the infarcted heart. Journal of the American College of Cardiology 63, 2862 (Jul. 1, 2014).

27. V. A. Ploplis et al., Effects of disruption of the plasminogen gene on thrombosis, growth, and health in mice. Circulation 92, 2585 (Nov. 1, 1995).

28. T. A. Drixler et al., Plasminogen mediates liver regeneration and angiogenesis after experimental partial hepatectomy. The British journal of surgery 90, 1384 (November, 2003).

29. J. Romer et al., Impaired wound healing in mice with a disrupted plasminogen gene. Nature medicine 2, 287 (March, 1996).

30. M. Yuasa et al., Fibrinolysis is essential for fracture repair and prevention of heterotopic ossification. J Clin Invest 125, 3117 (Aug. 3, 2015).

31. J. A. Bezerra et al., Plasminogen deficiency leads to impaired remodeling after a toxic injury to the liver. Proceedings of the National Academy of Sciences of the United States of America 96, 15143 (Dec. 21, 1999).

32. Baker B F, Lot S S, Condon T P, et al. 2'-O-(2-Methoxy)ethyl-modified anti-intercellular adhesion molecule 1 (ICAM-1) oligonucleotides selectively increase the ICAM-1 mRNA level and inhibit formation of the ICAM-1 translation initiation complex in human umbilical vein endothelial cells. The Journal of biological chemistry. 1997; 272(18):11994-2000.

33. N. Deconinck, B. Dan, Pathophysiology of duchenne muscular dystrophy: current hypotheses. Pediatric neurology 36, 1 (January, 2007).

34. M. Suelves et al., uPA deficiency exacerbates muscular dystrophy in MDX mice. The Journal of cell biology 178, 1039 (Sep. 10, 2007).

35. V. Y. Lounev et al., Identification of progenitor cells that contribute to heterotopic skeletogenesis. The Journal of bone and joint surgery. American volume 91, 652 (Mar. 1, 2009).

36. H. A. Cole et al., Fibrin accumulation secondary to loss of plasmin-mediated fibrinolysis drives inflammatory osteoporosis in mice. Arthritis & rheumatology 66, 2222 (August, 2014).

37. F. Lluis et al., Urokinase-dependent plasminogen activation is required for efficient skeletal muscle regeneration in vivo. Blood 97, 1703 (Mar. 15, 2001).

38. M. Suelves et al., Plasmin activity is required for myogenesis in vitro and skeletal muscle regeneration in vivo. Blood 99, 2835 (Apr. 15, 2002).

39. R. J. D. a. G. A. M. F. Marshall R. Urist, Bone Cell Differentiation and Growth Factors Science 220, 680 (May 13, 1983).

40. T. E. Douglas et al., Enzymatically induced mineralization of platelet-rich fibrin. Journal of biomedical materials research. Part A 100, 1335 (May, 2012).

41. R. G. Russell, Bisphosphonates: the first 40 years. Bone 49, 2 (July, 2011).

42. T. H. Bugge et al., Loss of fibrinogen rescues mice from the pleiotropic effects of plasminogen deficiency. Cell 87, 709 (Nov. 15, 1996).

43. B. Vidal et al., Amelioration of Duchenne muscular dystrophy in mdx mice by elimination of matrix-associated fibrin-driven inflammation coupled to the alphaMbeta2 leukocyte integrin receptor. Human molecular genetics 21, 1989 (May 1, 2012).

44. Y. Kanno et al., Lack of alpha2-antiplasmin improves cutaneous wound healing via over-released vascular endothelial growth factor-induced angiogenesis in wound lesions. Journal of thrombosis and haemostasis: JTH 4, 1602 (July, 2006).

45. N. Khalil, S. Corne, C. Whitman, H. Yacyshyn, Plasmin regulates the activation of cell-associated latent TGF-beta 1 secreted by rat alveolar macrophages after in vivo bleomycin injury. American journal of respiratory cell and molecular biology 15, 252 (August, 1996).

46. V. A. Ploplis, E. L. French, P. Carmeliet, D. Collen, E. F. Plow, Plasminogen deficiency differentially affects recruitment of inflammatory cell populations in mice. Blood 91, 2005 (Mar. 15, 1998).

47. D. Roth et al., Plasmin modulates vascular endothelial growth factor-A-mediated angiogenesis during wound repair. Am J Pathol 168, 670 (February, 2006).

48. J. Schoenecker et al., 2010 Young Investigator Award winner: Therapeutic aprotinin stimulates osteoblast proliferation but inhibits differentiation and bone matrix mineralization. Spine 35, 1008 (Apr. 20, 2010).

49. J. A. Yee, L. Yan, J. C. Dominguez, E. H. Allan, T. J. Martin, Plasminogen-dependent activation of latent transforming growth factor beta (TGF beta) by growing cultures of osteoblast-like cells. Journal of cellular physiology 157, 528 (December, 1993).

50. Nabeshima Y. [Discovery of alpha-Klotho and FGF23 unveiled new insight into calcium and phosphate homeostasis]. Clin Calcium. 2008;18(7):923-34.

51. Nabeshima Y. [Regulation of calcium homeostasis by alpha-Klotho and FGF23]. Clin Calcium. 2010;20(11): 1677-85.

52. Christensen B, Schack L, Klaning E, Sorensen E S. Osteopontin is cleaved at multiple sites close to its integrin-binding motifs in milk and is a novel substrate for plasmin and cathepsin D. The Journal of biological chemistry. 2010; 285(11):7929-37.

53. M. Herrmann et al., Clearance of fetuin-A-containing calciprotein particles is mediated by scavenger receptor-A. Circulation research 111, 575 (Aug. 17, 2012).

54. S. A. Steitz et al., Osteopontin inhibits mineral deposition and promotes regression of ectopic calcification. Am J Pathol 161, 2035 (December, 2002).

55. V. A. Ploplis, E. L. French, P. Carmeliet, D. Collen, E. F. Plow, Plasminogen deficiency differentially affects recruitment of inflammatory cell populations in mice. Blood 91, 2005 (1998).

56. R. Das, S. Ganapathy, M. Settle, E. F. Plow, Plasminogen promotes macrophage phagocytosis in mice. Blood 124, 679 (Jul. 31, 2014).

57. P. M. Henson, The immunologic release of constituents from neutrophil leukocytes. II. Mechanisms of release during phagocytosis, and adherence to nonphagocytosable surfaces. J Immunol 107, 1547 (December, 1971).

58. A. K. McNally, J. M. Anderson, Macrophage fusion and multinucleated giant cells of inflammation. Advances in experimental medicine and biology 713, 97 (2011).

59. P. M. Henson, Schwartzmann, N. A., and Zoanolari, B., Ed., Inflammation, Basic Principles and Clinical Correlates, (Raven Press, ed. 1st, 1998), 1st.

60. P. B. Yu et al., BMP type I receptor inhibition reduces heterotopic [corrected] ossification. Nature medicine 14, 1363 (December, 2008).

61. J. Schneiderman et al., Increased type 1 plasminogen activator inhibitor gene expression in atherosclerotic human arteries. Proceedings of the National Academy of Sciences of the United States of America 89, 6998 (Aug. 1, 1992).

62. D. T. Eitzman, R. J. Westrick, Z. Xu, J. Tyson, D. Ginsburg, Plasminogen activator inhibitor-1 deficiency protects against atherosclerosis progression in the mouse carotid artery. Blood 96, 4212 (Dec. 15, 2000).

63. Q. Xiao et al., Plasminogen deficiency accelerates vessel wall disease in mice predisposed to atherosclerosis. Proceedings of the National Academy of Sciences of the United States of America 94, 10335 (Sep. 16, 1997).

64. M. Eren et al., PAI-1-regulated extracellular proteolysis governs senescence and survival in Klotho mice. Proceedings of the National Academy of Sciences of the United States of America 111, 7090 (May 13, 2014).

65. K. Tsuji et al., BMP2 activity, although dispensable for bone formation, is required for the initiation of fracture healing. Nat Genet 38, 1424 (December, 2006).

66. L. M. Cooley, R. J. Goss, The effects of transplantation and x-irradiation on the repair of fractured bones. Am J Anat 102, 167 (March, 1958).

67. F. De Luca et al., Retinoic acid is a potent regulator of growth plate chondrogenesis. Endocrinology 141, 346 (January, 2000).

68. C. A. Lewis, R. M. Pratt, J. P. Pennypacker, J. R. Hassell, Inhibition of limb chondrogenesis in vitro by vitamin A: alterations in cell surface characteristics. Dev Biol 64, 31 (May, 1978).

69. A. M. Standeven et al., Retinoid-induced epiphyseal plate closure in guinea pigs. Fundam Appl Toxicol 34, 91 (November, 1996).

70. J. Li et al., Concentration of bisphosphonate (incadronate) in callus area and its effects on fracture healing in rats. Journal of bone and mineral research : the official journal of the American Society for Bone and Mineral Research 15, 2042 (October, 2000).

71. H. A. Cole et al., Differential development of the distal and proximal femoral epiphysis and physis in mice. Bone 52, 337 (January, 2013).

72. G. D. H. Stephanie N. Moore, Emily N. Smith, Nicholas A. Mignemi, Rivka C. Ihejirika, Masato Yuasa, Justin M. M. Cates, Xulei Lui, Jonathan G. Schoenecker, Validation of Radiography-Based Quantification Designed to Longitudinally Monitor Cardiotoxin-Induced Heterotopic Ossification in a Murine Model. PloS one, (Submitted and in Review Feb. 12, 2016).

73. M. J. Flick, X. Du, J. L. Degen, Fibrin(ogen)-alpha M beta 2 interactions regulate leukocyte function and innate immunity in vivo. Experimental biology and medicine 229, 1105 (December, 2004).

74. W. A. Knaus, E. A. Draper, D. P. Wagner, J. E. Zimmerman, APACHE II: a severity of disease classification system. Crit Care Med 13, 818 (October, 1985).

75. T. H. Wong, B. H. Tan, M. L. Ling, C. Song, Multi-resistant Acinetobacter baumannii on a burns unit-clinical risk factors and prognosis. Burns 28, 349 (June, 2002).

76. S. Hettiaratchy, R. Papini, Initial management of a major burn: I-overview. BMJ 328, 1555 (Jun. 26, 2004).

77. Tiffee J C, Aufdemorte T B. Markers for macrophage and osteoclast lineages in giant cell lesions of the oral cavity. J Oral Maxillofac Surg. 1997;55(10):1108-12; discussion 12-3.

78. Pisoni G, D'Amelio P, Sassi F, et al. Multinucleated giant cells with an osteoclast phenotype derived from caprine peripheral blood mononuclear cells. Vet J. 2011;189(3): 361-3.

79. Park J K, Askin F, Giles J T, Halushka M K, Rosen A, Levine S M. Increased generation of TRAP expressing multinucleated giant cells in patients with granulomatosis with polyangiitis. PloS one. 2012;7(8):e42659.

80. Park J K, Rosen A, Saffitz J E, et al. Expression of cathepsin K and tartrate-resistant acid phosphatase is not confined to osteoclasts but is a general feature of multinucleated giant cells: systematic analysis. Rheumatology (Oxford). 2013;52(8):1529-33.

81. Molligan J, Mitchell R, Schon L, et al. Influence of Bone and Muscle Injuries on the Osteogenic Potential of Muscle Progenitors: Contribution of Tissue Environment to Heterotopic Ossification. Stem Cells Transl Med. 2016.

82. A. F. Brooker, J. W. Bowerman, R. A. Robinson, L. H. Riley, Jr., Ectopic ossification following total hip replacement. Incidence and a method of classification. The Journal of bone and joint surgery. American volume 55, 1629 (December, 1973).

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A method for reducing or preventing soft tissue calcification in a subject, comprising administering an effective soft tissue calcification reducing or preventing amount of, to a subject in need thereof, a plasmin(ogen) and a downregulator of at least one plasmin inhibitor; said subject having an acquired plasmin deficiency, and said subject having a severe injury;
   wherein the at least one plasmin inhibitor includes α2-antiplasmin; and wherein the downregulator is an α2-antiplasmin antisense oligonucleotide;
   further comprising administration of an antifibronolytic provided that the administration of the antifibronolytic is stopped within three days following said administration of at least one of plasmin(ogen) and a downregulator of at least one plasmin inhibitor.

2. The method of claim 1, wherein the plasmin(ogen) is natural plasmin(ogen).

3. The method of claim 1, wherein the plasmin(ogen) is recombinant plasmin(ogen).

4. The method of claim 1, further comprising administering the compound at the time of or subsequent to muscle injury.

5. The method of claim 1, wherein the step of administering is subsequent to the severe injury.

6. A method for reducing or preventing soft tissue calcification in a subject, comprising administering least one of plasmin(ogen) and a downregulator of α2-antiplasmin to a subject in need thereof, wherein the subject does not have an inherited plasmin deficiency, provided that the method comprises administering at least the downregulator of α2-antiplasmin, and wherein the downregulator of α2-antiplasmin is an α2-antiplasmin antisense oligonucleotide;
   further comprising administration of an antifibronolytic provided that the administration of the antifibronolytic is stopped within three days following said administration of at least one of plasmin(ogen) and a downregulator of at least one plasmin inhibitor.

7. A method of treating a traumatic skeletal muscle injury in a subject, comprising:
- administering an effective muscle dystrophic calcification preventing or reducing amount to the subject a composition comprising a plasmin(ogen) and a downregulator of at least one plasmin inhibitor;
- wherein the at least one plasmin inhibitor includes α2-antiplasmin; and wherein the downregulator is an α2-antiplasmin antisense oligonucleotide;
- further comprising administration of an antifibronolytic provided that the administration of the antifibronolytic is stopped within three days following said administration of at least one of plasmin(ogen) and a downregulator of at least one plasmin inhibitor.

8. The method of claim 7, wherein the injury is burn, blast, crush, orthopedic procedures.

9. The method of claim 7, wherein the plasmin(ogen) is natural plasmin(ogen).

10. The method of claim 7, wherein the plasmin(ogen) is recombinant plasmin(ogen).

11. The method of claim 7, further comprising administering the compound at the time of or subsequent to muscle injury.

* * * * *